(12) United States Patent
Van Eijk et al.

(10) Patent No.: US 8,460,866 B2
(45) Date of Patent: Jun. 11, 2013

(54) HIGH THROUGHPUT SEQUENCE-BASED DETECTION OF SNPS USING LIGATION ASSAYS

(75) Inventors: Michael Josephus Theresia Van Eijk, Herpen (NL); Rene Cornelis Josephus Hogers, Ede (NL)

(73) Assignee: Keygene N.V., Wageningen (NL)

( * ) Notice: Subject to any disclaimer, the term of this patent is extended or adjusted under 35 U.S.C. 154(b) by 0 days.

(21) Appl. No.: 12/281,193

(22) PCT Filed: Mar. 1, 2007

(86) PCT No.: PCT/NL2007/000055
§ 371 (c)(1),
(2), (4) Date: Feb. 6, 2009

(87) PCT Pub. No.: WO2007/100243
PCT Pub. Date: Sep. 7, 2007

(65) Prior Publication Data
US 2009/0215633 A1    Aug. 27, 2009

Related U.S. Application Data

(60) Provisional application No. 60/777,514, filed on Mar. 1, 2006.

(51) Int. Cl.
*C12Q 1/68* (2006.01)
(52) U.S. Cl.
USPC .......................................................... 435/6.1
(58) Field of Classification Search
None
See application file for complete search history.

(56) References Cited

U.S. PATENT DOCUMENTS 6,027,889 A * 2/2000 Barany et al. ................. 435/6.12
6,124,092 A * 9/2000 O'Neill et al. .................... 435/6
7,935,488 B2   5/2011 Zabeau et al.

FOREIGN PATENT DOCUMENTS

| EP | 1130113 A1 * | 9/2001 |
|---|---|---|
| EP | 1319718 | 6/2003 |
| EP | 1602733 | 12/2005 |
| WO | WO 2004/076692 | 9/2004 |
| WO | WO 2005/021794 | 3/2005 |
| WO | WO 2005/026389 | 3/2005 |
| WO | WO 2005021794 A2 * | 3/2005 |

OTHER PUBLICATIONS

Stratagene ("Gene Characterization Kits" 1988).*
Marguiles et al. (Nature. Sep. 15, 2005;437(7057):376-80. Epub Jul. 31, 2005).*
International Search Report for International Application No. PCT/NL/000055, dated Jul. 6, 2007 (3 pgs.).
Accelerated Examination Support Document, filed in the USPTO on Oct. 5, 2010 in U.S. Appl. No. 12/484,541.
Baird, et al., "Rapid SNP Discovery and Genetic Mapping Using Sequenced RAD Markers", *PLoS ONE*, Oct. 2008, vol. 3, issue 10, e3376, pp. 1-7.
Lewis, et al., "High-Density Detection of Restriction-Site-Associated DNA Markers for Rapid Mapping of Mutated Loci in Neurospora", *Genetics*, Oct. 2007, vol. 177, pp. 1163-1171.
Miller, et al., "Rapid and cost-effective polymorphism identification and genotyping using restriction site associated DNA (RAD) markers", *Genome Research*, 2007, vol. 17, pp. 240-248.
Miller, et al., "RAD marker microarrays enable rapid mapping of zebrafish mutations", *Genome Biology*, 2007, vol. 8, Issue 6, Article R105.

* cited by examiner

*Primary Examiner* — Christopher M. Babic
(74) *Attorney, Agent, or Firm* — Foley & Lardner LLP

(57) ABSTRACT

Method for the detection the presence or absence of one or more target sequences in one or more samples based on oligonucleotide ligation assays with a variety of ligatable probes containing identifiers and the subsequent identification of the identifiers in the amplicons or ligated probes using high throughput sequencing technologies.

23 Claims, 15 Drawing Sheets

Uni- or bi-directional Sequencing by synthesis

FIG 12 Alelle specific extension prior to ligation

HIGH THROUGHPUT SEQUENCE-BASED DETECTION OF SNPS USING LIGATION ASSAYS

FIELD OF THE INVENTION

The present invention relates to the field of molecular biology and biotechnology. In particular the invention relates to the field of nucleic acid detection, more in particular to the design and composition of (collections) of probes that can be used for the high throughput detection of nucleic acids. The invention also relates to methods for the detection of nucleic acids using the probes and compositions. The invention further provides for probes that are capable of hybridising to a target sequence of interest, primers for the amplification of ligated probes, use of these probes and primers in the identification and/or detection of nucleotide sequences that are related to a wide variety of genetic traits and genes and kits of primers and/or probes suitable for use in the method according to the invention. The invention finds applicability in the field of the high throughput detection of target nucleotide sequences, whether from artificial, plant, animal or human origin or combinations thereof. The invention finds particular application in the field of high throughput genotyping.

BACKGROUND OF THE INVENTION

There is a rapidly growing interest in the detection of specific nucleic acid sequences. This interest has not only arisen from the recently disclosed draft nucleotide sequence of the human genome and many other genomes and the presence therein, as well as in the genomes of many other organisms, of an abundant amount of single nucleotide polymorphisms (SNP) and small insertion/deletions (indel) polymorphisms, but also from marker technologies (such as AFLP), SNPWave and the general recognition of the relevance of the detection of specific nucleic acid sequences as an indication of, for instance, genetically inheritable diseases. The detection of the various alleles of the breast cancer gene BRCA 1 to screen for susceptibility for breast cancer is just one of numerous examples. The recognition that the presence of single nucleotide substitutions and indels in genes provide a wide variety of information has also attributed to this increased interest. It is now generally recognised that these single nucleotide substitutions are one of the main causes of a significant number of monogenically and multigenically inherited diseases, for instance in humans, or are otherwise involved in the development of complex phenotypes such as performance traits in plants and livestock species. Thus, single nucleotide substitutions are in many cases also related to or at least indicative of important traits in humans, plants and animal species.

Analysis of these single nucleotide substitutions and indels will result in a wealth of valuable information, which will have widespread implications on medicine and agriculture in the widest possible terms. It is for instance generally envisaged that these developments will result in patient-specific medication. To analyse these genetic polymorphisms, there is a growing need for adequate, reliable and fast methods that enable the handling of large numbers of samples and large numbers of (predominantly) SNPs in a high throughput fashion, without significantly compromising the quality of the data obtained. One of the principal methods used for the analysis of the nucleic acids of a known sequence is based on annealing two probes to a target sequence and, when the probes are hybridised adjacently to the target sequence, ligating the probes.

The OLA-principle (Oligonucleotide Ligation Assay) has been described, amongst others, in U.S. Pat. No. 4,988,617 (Landegren et al.). This publication discloses a method for determining the nucleic acid sequence in a region of a known nucleic acid sequence having a known possible mutation. To detect the mutation, oligonucleotides are selected to anneal to immediately adjacent segments of the sequence to be determined. One of the selected oligonucleotide probes has an end region wherein one of the end region nucleotides is complementary to either the normal or to the mutated nucleotide at the corresponding position in the known nucleic acid sequence. A ligase is provided which covalently connects the two probes when they are correctly base paired and are located immediately adjacent to each other. The presence, absence or amount of the linked probes is an indication of the presence of the known sequence and/or mutation.

Other variants of OLA-based techniques have been disclosed inter alia in Nilsson et al. Human mutation, 2002, 19, 410-415; Science 1994, 265: 2085-2088; U.S. Pat. No. 5,876,924; WO 98/04745; WO 98/04746; U.S. Pat. No. 6,221,603; U.S. Pat. No. 5,521,065; U.S. Pat. No. 5,962,223; EP 185494B1; U.S. Pat. No. 6,027,889; U.S. Pat. No. 4,988,617; EP 246864B1; U.S. Pat. No. 6,156,178; EP 745140 B1; EP 964704 B1; WO 03/054511; US 2003/0119004; US 2003/0190646; EP 1313880; US 2003/0032016; EP 912761; EP 956359; US 2003/108913; EP 1255871; EP 1194770; EP 1252334; WO96/15271; WO97/45559; US2003/0119004A1; U.S. Pat. No. 5,470,705.

Particular advancements in the OLA techniques have been reported by Keygene, Wageningen, the Netherlands. In WO 2004/111271, WO2005/021794, WO2005/118847 and WO03/052142, they have described several methods and probe designs that improved the reliability of oligonucleotide ligation assays. These applications further disclose the significant improvement in multiplex levels that can be achieved. However, all the above publications have as a disadvantage that they are based on electrophoretic- or array-based detection methods. A further disadvantage is the wide variation in length of the probes used, which may leads to less consistent amplification.

It is clear that there is a continuing need for oligonucleotide probes that combine the advantages and avoid the specific disadvantages of the various ligation probe types and detection methods known in the art. There is also a need for further improvement of the technology by providing probes that have additional advantages. It is one of the goals of the present invention to provide such probes. It is another goal of the present invention to avoid the disadvantages of the commonly known probes as mentioned hereinbefore. It is a further goal of the invention to provide for probes that are suitable for high throughput detection methods. It is also a goal of the present invention to provide for an efficient, reliable and/or high throughput method for the detection of target nucleotide sequences, preferably by performing oligonucleotide ligation assays.

The present inventors have set out to eliminate or at least diminish the existing problems in the art while at the same time attempting to maintain the many advantageous aspects thereof, and to further improve the technology. Other problems in the art and solutions provided thereto by the present invention will become clear throughout the description, the figures and the various embodiments described herein.

SUMMARY OF THE INVENTION

The present inventors have been able to combine novel high throughput sequencing technologies with the versatility of oligonucleotide ligation based assays. In particular, the invention relates to a method for high throughput detection of target nucleotide sequences based on oligonucleotide ligation assays, wherein the probes used in the ligation assays are modified such that a high throughput sequencing method can be used to unequivocally reveal the present absence of the amount of the one or more target nucleotide sequences.

Thus, the present inventors have found that by incorporation of a unique oligonucleotide identifier in at least one of the probes that are used in the OLA-assay for the detection of each target sequence in the sample and the subsequent detection of that identifier after the ligation and amplification steps by high throughput sequencing methods provides for a very efficient and reliable improvement of the existing technology. Contrary to the known probes in the art, whether linear or circularizable, the probes used in the method of the present invention can all have the same or very similar length. This uniform length is advantageous when the ligated probes are amplified as the amplification efficiencies for all ligated probes are similar, whereas with different length of the ligated probes, it has been observed that amplification efficiency may differ widely, thus compromising the reliability of the assay as a whole. The uniform length also facilitates the detection as the identifier is located at the same position for all ligated probes. By improving the OLA assays in this manner, a significant step is made in providing increasingly uniform assays that are easy to design for a specific target sequence, are able to reliably discriminate between target sequences or samples and can be performed in a high throughput, highly multiplexed fashion.

In certain embodiments, methods for the high throughput detection of one or more target nucleotide sequences are provided. In certain embodiments, the method provides the high throughput detection of one or more target nucleotide sequences that may be derived from one or more samples. In certain embodiments, the method comprises providing for each target nucleotide sequence a first probe and a second probe.

In certain embodiments the first probe comprises a target specific section at its 3'-end. In certain embodiments, the first probe further comprises a first tag section. In certain embodiments, the first tag section is non-complementary to the target nucleotide sequence. In certain embodiments, the first tag section further comprises a first primer binding sequence.

In certain embodiments, the second probe comprises a second target specific section at its 5'-end. In certain embodiments, the second probe comprises a second tag section. In certain embodiments, the second tag section is non-complementary to the target nucleotide sequence. In certain embodiments, the second tag section further comprises a second primer binding sequence. In certain embodiments, the first or the second tag section contains an identifier sequence. In certain embodiments, both the first and second tag section contain an identifier sequence. In certain embodiments, the identifier sequence is located between the first primer binding sequence and the first target specific sequence. In certain embodiments, the identifier is located between the second primer binding sequence and the second target specific sequence.

In certain embodiments the first and second probes are allowed to hybridise to the target sequence in the sample. The respective first and second target specific sections of the probes are hybridised to preferably essentially adjacent sections on the target sequence, although in some embodiments a gap may be present between the two sections. In certain embodiments, the first and second probes are ligated i.e. connected to each other. The ligation of the first and second probe provides for ligated probes.

In certain embodiments the ligated probes are amplified to provide amplicons. In certain embodiments one or more primers are used in the amplification. In certain embodiments a first and, in certain embodiments, a second primer are used for the amplification.

In certain embodiments a first and, in certain embodiments a second primer can be used which, independently, may contain a restriction enzyme recognition site to provide amplicons. The amplicons are digested with the respective restriction enzymes for which recognition sites are present in the first and, in certain embodiments the second primer. Sequences for a third and, in certain embodiments a fourth primer, can subsequently be ligated to the digested amplicons to provide a template for amplification. In certain embodiments the third and second and, in certain embodiments the third and fourth primer are used in the amplification.

In certain embodiments the ligated probes or, in certain embodiments, the amplicons derived from amplification of the ligated probes, are subjected to high throughput sequencing technologies to determine at least part of the nucleotide sequence of the ligated probes or amplicons. In certain embodiments the part(s) of the nucleotide sequence that is(are) determined by subjecting the ligated probes or amplicons to high throughput sequencing technologies at least includes the identifier sequence(s).

In certain embodiments the presence of the target nucleotide sequence in the sample is identified by determination of the presence or absence of the associated identifier sequence in the nucleotide sequence.

BRIEF DESCRIPTION OF THE DRAWINGS

The present invention is illustrated by the following figures:

In FIG. 1, different probe types (A, B, C, D, E, F), are schematically illustrated vis-à-vis a target nucleotide sequence (T) of interest, carrying an A/C polymorphism. Various components of the probes have been depicted, using identical depictions throughout the figures.

FIG. 1A illustrates a linear probe type, wherein a first probe (1) comprises a first target specific section (TS1) and a first tag section comprising a first identifier (ID1) and a first primer binding sequence (PBS1), capable of annealing to a first primer (P1). A second probe (2) comprises a second target specific section (TS2) and a second tag section comprising a second identifier (ID2) and a second primer binding sequence (PBS2), capable of annealing to a second-primer (P2). In embodiments for allele specific detection, TS2 may contain, preferably at its 3' end, an allele specific nucleotide (G or T), together with a different identifier (ID2 or ID2'). The locus allele combination may then be determined (genotyped) by detection of the presence or absence of the combination of ID1 with ID2 or ID2'. In similar manner, all allelic variants of a polymorphism can be genotyped. Allele-specific probes can be designed for the other disclosed probe type in a similar fashion.

FIG. 1B illustrates a circularizable probe type, wherein the circularizable probe comprises a first target specific section (TS1) and a second target specific section (TS2), each located at the end (the respective 3' and 5' ends) of the circularizable probe and a tag section comprising a first identifier (ID1), a first primer binding sequence (PBS1) that is capable of annealing to a first primer (P1), a second primer binding sequence (PBS2) that is capable of annealing to a second primer (P2) and an optional second identifier (ID2). ID1 and ID2 may be located adjacent or not. In certain embodiments, the use of this probe type is coupled with an exonuclease treatment to remove unligated probes that may give rise to false-positive genotyping. In certain designs, the combination ID1 and ID2 may represent locus allele combinations. Amplification of circularised probes will results in short amplicons that can be sequenced and determination of the presence of ID1 and/or ID2 provides positive genotyping of the desired polymorphism.

FIG. 1C illustrates an alternative circularizable probe type. The probe contains the same components, but the relative positioning and orientation of ID1, ID2, PBS1 and PBS2 is such that amplification will only occur when the probe is circularised. This avoids any removal of unligated probes.

FIG. 1D illustrates a linear probe type that is similar to the linear type of FIG. 1A. In addition thereto clamp sections C1 and C2 have been incorporated in the tag section, preferably at the end, but they may also be located between ID and TS or between PBS and ID. C1 and C2 will anneal/hybridize to each other, thereby mimicking the padlock behaviour and in particular the improved hybridisation kinetics compared to conventional linear probe types (FIG. 1A), while at the same time concatenation of the amplicons of the probe type of FIG. 1B or C can be avoided.

FIG. 1E illustrates the conformation of the compound probe and the elongation thereof. The first probe (1) preferably consists of a first target specific section (TS1). The second probe (2) comprises a second target specific section (TS2) and a second tag section comprising a second identifier (ID2) and a second primer binding sequence (PBS2). After or simultaneously with the hybridisation/ligation step, a compound probe (C) is annealed to part of TS1 with a section that is capable of hybridizing to (part of) the first target specific section (TSP1). (C) further contains a section that contains a primer binding section (PBS1) capable of binding to a primer (P1). Elongation of the compound probe yields a section complementary to the second target specific section (TSP2), complementary to the second identifier cID2) and complementary to the second primer binding sequence (cPBS2) capable of annealing to primer cP2. Amplification using primers P1 and cP2 yields amplicons that can be sequenced.

FIG. 1F illustrates the conformation of a set of asymmetric probes. The first probe (1) contains a target specific section (TS1) and is exonuclease resistant (star). The second probe (2) contains a second target specific section (TS2) and a tag section that contains two primer binding sites (PBS1 and PBS2, respectively) and a second identifier ID2 located between PBS1 and PBS2. Successful ligation and removal of unligated probes followed by amplification provided amplicons that can be sequenced.

DETAILED DESCRIPTION OF THE INVENTION

Figure 1:
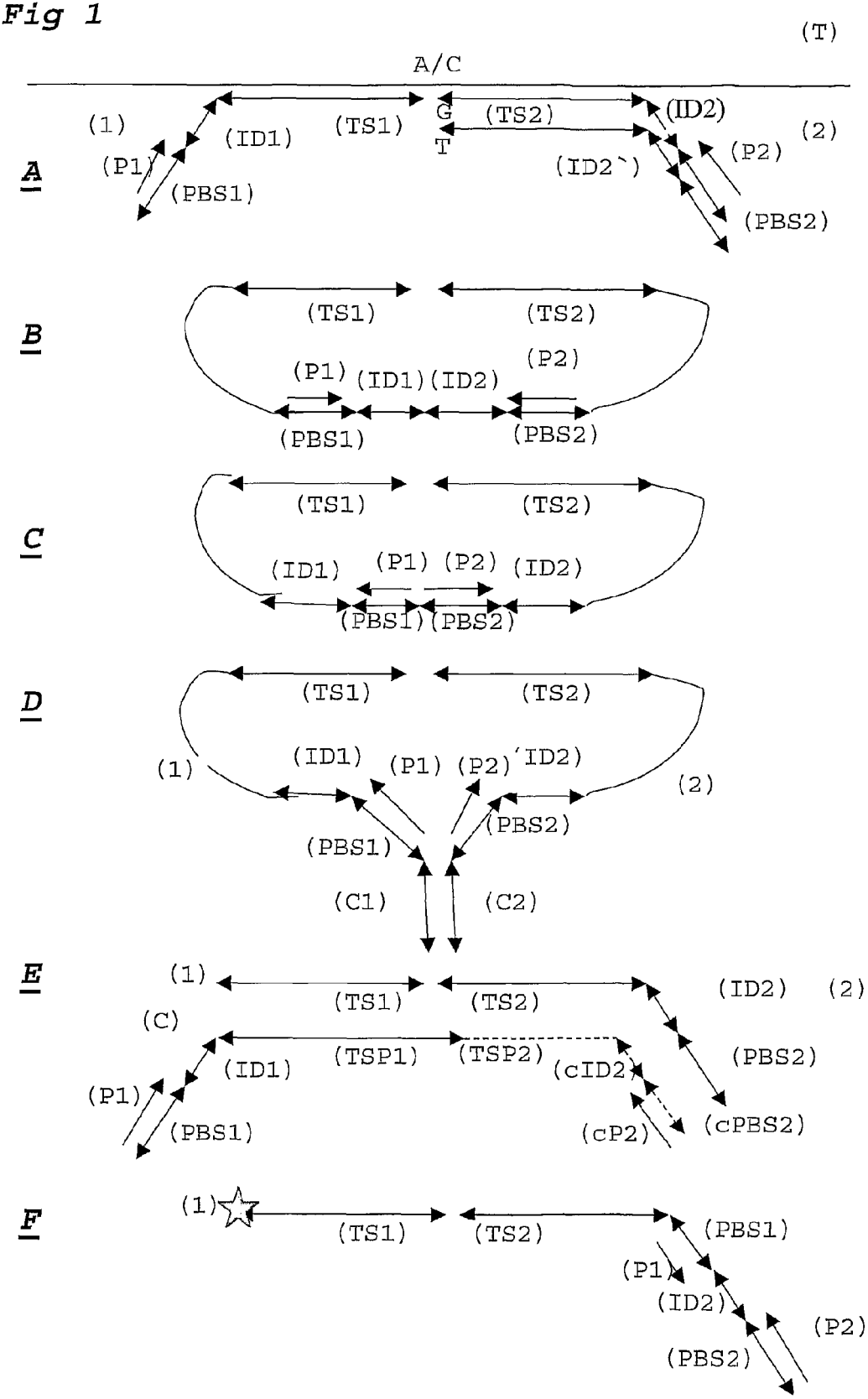
FIG. 1.

The present invention in a first aspect pertains to a method for the high throughput detection of one or more target nucleotide sequences in one or more samples, the method comprising the steps of:

(a) providing for each target nucleotide sequence a first probe and a second probe, wherein
   the first probe comprises a target specific section at its 3' end and a first tag section that is non-complementary to the target nucleotide sequence and that comprises a first primer binding sequence,
   the second probe comprises a second target specific section at its 5' end and a second tag section that is non-complementary to the target nucleotide sequence and that comprises a second primer binding sequence,
   wherein the first or second tag section, or both, contain(s) an identifier sequence that is located between the respective first or second primer binding sequence and the respective first or second target specific section, (b) allowing the first and second probe to hybridise to the target sequence, (c) ligating the first and second probe when the respective target specific sections of the probes are hybridised to essentially adjacent sections on the target sequence to provide ligated probes, (d) optionally, amplifying the ligated probes with a first and a second primer to provide amplicons, (e) subjecting the ligated probes or amplicons to high throughput sequencing technology to determine at least part of the nucleotide sequence, at least including the identifier sequence, of the ligated probes or the amplicons, (f) identifying the presence of the target nucleotide sequence in the sample by determination of the presence or absence of the identifier sequence in the nucleotide sequence of step (e).

The method starts with the provision of one or more samples (that may be combined or pooled) that may contain the sequence of interest. To this sample, the set of probes is added (for each target sequence different sets of probes may be provided) and the target specific sections of the probes are allowed to hybridise to the target sequence under suitable conditions. After hybridisation, any probes hybridised adjacent on the target sequence are ligated to result in ligated probes. The ligated probes may be amplified or, alternatively, directly subjected to sequencing using high throughput sequencing methods based on sequencing by synthesis. With the sequencing step and the subsequent identification of the identifier, the presence of the target sequence in the sample is determined and the genotyping is completed.

One aspect of the present invention pertains to the advantageous design of the probes used in the present invention. These probes will be discussed in more detail herein below. Another advantageous aspect of the invention resides in the connection between the state of the art high throughput sequencing technologies as a detecting platform for oligonucleotide ligation assays and the discriminatory power of the OLA-based assays. As currently known OLA assays have been devised only for detection platforms that are based on length/mobility separation (i.e. electrophoretic analysis), hybridization (array-based) or mass determination (mass-spectrometry/MALDI-TOF), whereas no suitable probes have been developed that can be used in high throughput sequencing detection platforms. Applicants have observed that apart from innovations in probe design, also the methods of performing OLA assays in combination with high throughput sequencing requires serious amendments to both probes and procedures.

Target Nucleotide Sequence

In its widest definition, the target sequence may be any nucleotide sequence of interest. The target sequence can be any sequence of which its determination/detection is desired, for instance because it is indicative, associated or representative of a certain ailment or genetic make up or disorder. The target sequence preferably is a nucleotide sequence that contains, represents or is associated with a polymorphism. The term polymorphism herein refers to the occurrence of two or more genetically determined alternative sequences or alleles in a population. A polymorphic marker or site is the locus at which sequence divergence occurs. Preferred markers have at least two alleles, each occurring at frequency of greater than 1%, and more preferably greater than 10% or 20% of a selected population. A polymorphic locus may be as small as one base pair.

Polymorphic markers include restriction fragment length polymorphisms, variable number of tandem repeats (VN-TR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wild type form. Diploid (and tetraploid/hexaploid) organisms may be homozygous or heterozygous for allelic forms. A diallelic polymorphism has two forms. A triallelic polymorphism has three forms. A single nucleotide polymorphism occurs at a polymorphic site occupied by a single nucleotide, which is the site of variation between allelic sequences. The site is usually preceded by and followed by highly conserved sequences of the allele (e.g., sequences that vary in less than $1/100$ or $1/1000$ members of the populations). A single nucleotide polymorphism usually arises due to substitution of one nucleotide for another at the polymorphic site. Single nucleotide polymorphisms can also arise from a deletion of a nucleotide or an insertion of a nucleotide relative to a reference allele. Other polymorphisms include (small) deletions or insertions of several nucleotides, referred to as indels. The process of analysing the particular genetic variations (polymorphisms) existing in an individual DNA sample using the presently described methods is sometimes referred to in this application as genotyping or SNP genotyping in the ace of single nucleotide polymorphisms.

DNA

In the nucleic acid sample, the nucleic acids comprising the target may be any nucleic acid of interest. Even though the nucleic acids in the sample will usually be in the form of DNA, the nucleotide sequence information contained in the sample may be from any source of nucleic acids, including e.g. RNA, polyA+ RNA, cDNA, genomic DNA, organellar DNA such as mitochondrial or chloroplast DNA, synthetic nucleic acids, DNA libraries (such as BAC libraries/pooled BAC clones), clone banks or any selection or combinations thereof. The DNA in the nucleic acid sample may be double stranded, single stranded, and double stranded DNA denatured into single stranded DNA. Denaturation of double stranded sequences yields two single stranded fragments one or both of which can be analysed by probes specific for the respective strands. Preferred nucleic acid samples comprise target sequences on cDNA, genomic DNA, restriction fragments, adapter-ligated restriction fragments, amplified adapter-ligated restriction fragments, AFLP® fragments or fragments obtained in an AFLP-template preamplification.

Samples

It is preferred that a sample contains two or more different target sequences, i.e. two or more refers to the identity rather than the quantity of the target sequences in the sample. In particular, the sample comprises at least two different target sequences, in particular at least 100, preferably at least 250, more preferably at least 500, more in particular at least 1000, preferably at least 2500, more preferably at least 5000 and most preferably at least 10000 additional target sequences. In practice, the number of target sequences in a sample that can be analysed is limited, among others, by the number of amplicons than can be detected. The presently employed detection methods allow for relative large numbers of target sequences.

Probe

The sections of the oligonucleotide probes that are complementary to the target sequence are designed such that for each target sequence in a sample, a pair of a first and a second probe is provided, whereby the probes each contain a section at their extreme end that is complementary to a part of the target sequence (a first and a second part of the target sequence, respectively) and the corresponding complementary parts of the target sequence are preferably located essentially adjacent to each other.

In certain embodiments, additional first and/or second probes can be provided, corresponding to different alleles of a locus. In certain embodiments, the allele specific nucleotide is located at the position of either the first or the second probe at which ligation is to occur, i.e. at the end of the target specific section (see FIG. 1A).

In certain embodiments, within a pair of oligonucleotide probes, the first oligonucleotide probe has a section at its (phosphorylated) 5'-end that is complementary to a first part of a target sequence and the second oligonucleotide probe has a section at its 3'-(hydroxyl)end that is complementary to a second part of the target sequence. Thus, when the pair of probes is annealed to complementary parts of a target sequence the 5'-end of the first oligonucleotide probe is essentially adjacent to the 3'-end of the second oligonucleotide probe such that the respective ends of the two probes may be ligated to form a phosphodiester bond or covalently connect in an other suitable fashion. In certain embodiments, within a pair of oligonucleotide probes, the first oligonucleotide probe has a section at its 3'-end that is complementary to a first part of a target sequence and the second oligonucleotide probe has a section at its 5'-end that is complementary to a second part of the target sequence. Thus, when the pair of probes is annealed to complementary parts of a target sequence, the 3'-end of the first oligonucleotide probe is essentially adjacent to the 5'-end of the second oligonucleotide probe such that the respective ends of the two probes may be ligated to form a phosphodiester bond or covalently connect in an other suitable fashion.

In certain embodiments, for each target sequence for which the presence, absence or amount in a sample is to be determined, a specific pair of first and second oligonucleotide probes is designed, each probe with a section complementary to the adjacent complementary part of each target sequence, as described above. Thus, in the method of the invention, for each target sequence that is present in a sample, a ligated probe or a corresponding (specific) amplicon may be obtained in the amplified sample. In certain embodiments, a multiplicity of first and second oligonucleotide probes complementary to a multiplicity of target sequences in a sample is provided. A pair of first and second oligonucleotide probes for a given target sequence in a sample will at least differ in nucleotide sequence from probe pairs for other target sequences or other samples, and may differ in length and/or mass from probe pairs for other targets (although, as outlined above, this is less preferred). More preferably, a probe pair for a given target will produce a ligated or connected probe and/or amplicon that differs in sequence from connected probes corresponding to other targets in the sample as described below.

Probe Variations
Padlock

In certain embodiments, of the invention, circularizable probes or padlock probes can be used. The first and second probes are then combined into one probe. The circularizable probe is a linear oligonucleotide that, when annealed to the target sequence, and when ligated, has a circular conformation that is topologically locked to the target sequence. In certain embodiments, an exonuclease treatment of the sample after the ligation step and prior to amplification, preferably PCR-amplification, serves to remove any non-ligated circular probes and to prevent any non-ligated probes from amplification. Circularizable probes are themselves known in the art, for instance from EP745140 or from Van Eijk et al, Nucleic Acids Research, 2004, 32, e47. The known probes are commonly amplified using rolling circle amplification or the polymerase chain reaction resulting in concatamers. Furthermore, the primer binding sites in the known circularizable probes are oriented such that the entire circularised probe is amplified including any target specific sections. In order to circumvent concatamer products during PCR amplification, a blocking modification can be incorporated in the ligation probe between the two primer binding sites of the type described in WO03/052142.

In certain embodiments, the primer binding sites in the present circularizable probes are oriented such that preferably only the section comprising the primer binding sites and the identifier is amplified and preferably the ligated target specific sections are not amplified. Preferably in combination with the exonuclease treatment to remove unligated circularizable probes, this provides amplicons of relatively short length compared to conventional amplicons obtained from conventionally amplifying circularised probes. This avoids the formation of large concatamers and further unnecessary amplification of the entire circularized probe.

In certain embodiments, the identifier is located essentially adjacent to one of the primer binding sequences, and preferably between the first and second primer binding site, such that upon amplification the amplicons at least comprises one of the two primer binding sites and the intermittent identifier. Subsequent high throughput sequencing of the amplicon will provide the sequence of the identifier and hence of the presence of the target sequence in the sample.

Keylock

In certain embodiments, for each given target sequence to be detected, preferably at least a pair of two probes is designed such that each probe in the pair is capable of hybridising to a part of the target sequence and the respective probes in the pair further each comprise a section that is complementary to a corresponding section of the other probe in the pair such that both probes are capable of hybridising to each other. The two probes in the pair are designed such that when hybridised to each other they are each also capable of hybridising to a target sequence. When hybridised to each other the two probes mimic or act as padlock probes when used in an oligonucleotide ligation assay for the detection of a target nucleotide sequence, whereas in the subsequent amplification and detection steps the probes function as a linear ligation product. This type of probe has been dubbed "Keylock" and is disclosed inter alia in WO2004111271.

In certain embodiments, the first oligonucleotide probe has a section at its 5'-end that is complementary to a first part of a target sequence and the second oligonucleotide probe has a section at its 3'-end that is complementary to a second part of the target sequence. In certain embodiments, the first oligonucleotide probe further comprises a clamp section that is capable of hybridising to a complementary clamp section located in the second oligonucleotide probe whereby the clamp sections are essentially non-complementary to the target sequence. In certain embodiments, the invention pertains to a method for determining the presence, absence of a target sequence or amounts of at least one target sequence in a sample as outlined herein, where the method comprises the steps of providing a pair of probes comprising clamp sections as outlined herein for each target sequence to be detected. In certain embodiments, the oligonucleotide probes are allowed to anneal to the target sequence, providing means for connecting the first and the second oligonucleotide probes and allowing first and second oligonucleotide probes to be connected to produce a connected probe corresponding to a target sequence in the sample.

The clamp section is preferably located at or near the end of the probe that is distal to the target section, i.e. when the target section is located at the 3' end, the clamp section is located more towards the 5' end and vice versa. The clamp section is not necessarily located most distal at the 5' end or 3' end; it may be followed by other sections as discussed herein elsewhere. The clamp sections are preferably designed such that they are not capable of hybridising to the target sections. The clamp sections of the first and second probe of the pair are preferably capable of hybridising to each other. The clamp sections are preferably designed such that two complementary clamp sections have a higher binding affinity for each other than the binding affinity of the target section of the probe for its complementary part in the target nucleotide sequence.

This means in practice that the clamp sections, when hybridised to each other, form a stronger duplex than the hybrid between the target section and its complement in the target nucleotide sequence and/or hybridization of complementary clamps takes place at higher temperatures than hybridisation of the target complementary section of the probes to the target. In other words, the hybridised clamp section denatures, under otherwise comparable conditions, at a higher temperature or higher stringency conditions than the denaturation temperature of the target complementary sections in the pair of probes. This allows to choose the conditions during the method of the invention such that the hybridised or locked clamp remains hybridised or closed at least until the probes are connected to produce a connected probe. The locked clamp can be opened by denaturing the (connected) probe at a temperature or under circumstances that allow the denaturation of the locked clamp.

A pair of probes having locked clamps expresses similar or identical hybridisation kinetics and behaviour as do circularizable or padlock probes. The two probes of a pair can be added separately after which the clamp sections are hybridised to each other in the sample or, alternatively, the two probes can be locked prior to being added to the sample.

In a preferred embodiment, the clamp has a denaturation temperature (or melting temperature, Tm) that exceeds the denaturation temperature of the target complementary sections in the pair of probes by at least 1 degree Celsius, preferably 5 degrees Celsius. more preferably 10 degrees Celsius greater than the lowest Tm of the T1 or T2 section. The denaturation temperature of a oligonucleotide sequence can calculated/estimated from the nucleotide composition using the general formula's for Tm=(4*G or C)+(2*A T) or Tm=(4*G/C)+2*A/T)−5C (Meinkoth et al. Anal. Biochem. (1984) 138: 267-284). Other formulas are likewise applicable as the essence lies in the difference in denaturation temperature between the sections (Tm[clamp]-Tm[target]). This can be achieved not only by varying the length of the clamp sections but also by varying the GC content of the clamp, as a GC basepair, increases Tm by about 2 degrees Celsius compared to an AT basepair.

A typical clamp section comprises 10 to 30, preferably 15 to 25 and more preferably 18 to 24 nucleotides. When the GC content is lower, this number of nucleotides may increase as long as the desired hybridisation characteristics are obtained. Alternatively modified nucleotides can be used that increase the hybridisation between the two clamp sections. Examples thereof are nucleotides that have improved hybridisation characteristics, such as Locked Nucleic Acids such as disclosed in WO 99/14226, WO 00/56748, WO 00/66604 and WO01/25478, Peptide Nucleic Acids or by other molecules that stabilise or enhance DNA hybridisation such as minor groove binders and other, such as those in described in EP 0 974 672.

The GC content of the clamp may vary, wherein the GC content of clamp section ranges from more than 50 to 100%, preferably more than 60%, more preferably more than 70%, most preferably more than 80% and is preferably in the range of 90-100%. Hence most clamp sections will contain A/T combinations on a more incidental or structural basis. A preferred group of clamp sections are GC enriched ZIP sequences (Iannone et al. (2000), Cytometry 39: pp. 131-140). Preferably the clamp section comprises at least one, preferably at least 2, 3, 4, or 5 nucleotides selected from the group consisting of G's and C's, more than each of T1 and T2.

In certain embodiments, when groups of pairs of probes are involved, a different clamp section may be provided for each pair of probes in the group. The clamp section is designed such that a clamp for a first pair of probes and clamps for a second or further pair of probes are distinguishable from each other and preferably do not cross hybridise under conditions used in the ligation assay. Each pair of probes comprises a unique clamp, thereby avoiding cross hybridisation between clamps of different pairs of probes in a sample. To this end the clamp section may comprise additional nucleotides or the oligonucleotide sequences of the clamp section can be unique within the group or a combination thereof, thereby providing for discrimination between two clamps in a group or in order to provide increase the number of possible non-cross binding clamp sequences for use in multiplex ligation assays. This latter embodiment enables the detection of multiple target sequences in one sample simultaneously. This embodiment also enables the detection of one or more different target sequences in multiple samples subsequently using the same collection of pairs of probes. This embodiment enables that the same group of pairs can be used over and over again for the detection of different target sequences.

Preferably, when using different clamps in a group of pairs of probes, these clamps have a Tm that is within a small range, preferably between about 60-90 degrees Celsius, more preferably between 65-88 degrees Celsius, most preferably between 70-85 degrees Celsius. As is known the hybridisation characteristics of nucleic acids are also influenced by the salt concentrations. As used herein, comparison of hybridisation characteristics in general or denaturation temperatures in particular of oligonucleotides is considered under comparable salt concentrations unless indicated otherwise. Alternative clamps that can be used in the present invention are nucleic acids that contain photodegradable links. After ligation, the photodegradable link is removed and the connected probe amplified and/or detected.

In certain embodiments, the probes of the present invention are equipped with such clamp sections. In certain embodiments, the clamp section of the first and/or the second probe or part thereof is rendered exonuclease resistant as outlined herein elsewhere for other probes. In certain embodiments, the clamp section or part thereof can be used for isolation of any unligated first probes and or connected probes based on hybridisation of the clamp section such as disclosed herein elsewhere for hybridisation based pullout or other hybridisation based isolation methods using glass slides, arrays, beads, paramagnetic particles etc. In certain embodiments, the clamp section is denatured prior to exonuclease treatment and/or isolation of unligated first probe or connected probes.

In the Keylock type probes, the identifier is located between the primer binding section and the target specific section of the probe. Both halves of a Keylock probe may be equipped with an identifier.

Compound Probe

In certain embodiments of the present invention, a set of probes are used that is described in WO2005021794. The target sequence is brought in to contact with a first and a second probe, wherein the first probe contains a first target specific section that is complementary to the target sequence and wherein the first probe preferably does not contain a first primer binding sequence in an optional first tag section. The second probe contains a second target specific section and a second tag section wherein the second tag section contains a second primer binding sequence. The second tag section may contain an identifier between the second primer binding sequence and the second target specific section. After, or simultaneously with, the hybridisation and ligation of the two probes, a compound probe is provided that contains a section that is capable of hybridizing to (part of) the first target specific section and further contains a section that contains a primer binding section. The compound probe hybridises to the ligated first and second probe. Elongation of the compound probe along the ligated first and second probe provides for the elongated compound probe that can subsequently be amplified using first and second primers that can bind to the first and second primer binding sites. The resulting amplicons can be detected using high throughput sequencing technologies as described herein and the target sequence in the sample can be identified by means of the presence or absence of the identifier.

Asymmetric Probes

In certain embodiments, a set of probes is used that is described in WO2005118847. In this embodiment, the target sequence is brought into contact with a first and a second probe. The first probe contains a first target specific section and preferably consists thereof, i.e. does not contain a first tag section that may comprise a first primer binding sequence. The first target specific section may, preferably at the end distal from the potential point of ligation, contain means that render the probe resistant against exonucleases such as biotin or modified nucleotides such as phosphoromonothioate, phosphorodithioate and phosphoroamidate modifications and PNAs and LNAs (see also WO2005118847 for more details in this respect). The second probe contains a second target specific section and a second tag section. The second tag section typically comprises a first and a second primer binding sequence and a intermittently located identifier. Successful hybridisation and ligation results in connected probes. An exonuclease step is performed to remove all unligated probes, i.e. the second probes. Amplification will only be accomplished for ligated probes that are rendered exonuclease resistant by the presence of the first probe. Amplification of the ligated probes with a set of a first and a second primer will result in the generation of short amplicons, mainly consisting of the two primers and the intermittent identifier. These short amplicons (and the identifier therein and consequently the associated target sequence) can be identified using the high throughput sequencing methods of the present invention.

Tag Section

The term tag section is used to denote those parts of the probes that are not capable of hybridizing to the target nucleotide sequences. The tag sections usually contain identifiers and primer binding sites and in some occasions, as outlined herein elsewhere, clamp sections.

Primer Binding Sequence

Primer binding sequences may be incorporated in the probes to facilitate amplification, whether linear or exponential. Primer binding sites are preferably located in other parts of the probe than in the target specific section, preferably in the tag section which is essentially non-complementary to the target sequence. Primer binding sites are capable of binding primers to initiate primer elongation or amplification. Preferably within a group of pairs of probes, the primer binding sites are universal, i.e. only a predetermined group of primer binding sites are incorporated in the probe to enable multiplex primer elongation or amplification from a limited number of primers, such as primers comprising one or more selective bases at their 3' end, such as are known from AFLP (EP 0 534 858). Between groups of pairs of probes, primer binding sites may be different. In certain embodiments, the Tm of primers capable of binding to the different primer binding sites may be different between groups of pairs of probes.

The function of identifier and primer binding sites in a probe can be combined and can be interrelated in the sense that a specific part of the probe may function as (part of) a primer binding site for (selective) primer elongation/amplification, and at the same or another time as (part of) an identifier to impart the desired and detection platform-based difference such as disclosed herein elsewhere.

Identifier Sequence

In certain embodiments, the oligonucleotide probe of the present invention further comprises an identifier or an identifier sequence. The identifier sequence is an oligonucleotide sequence of a variable sequence. The length of the identifier varies from 1 to 30, preferably from 2 to 20, more preferably from 3 to 10 and most preferred from 4 to 6 nucleotides. The identifier is a unique sequence. The unique character can be explained as a ZIP-coded sequence of the type as described by Iannone et al. (2000), Cytometry 39: pp. 131-140. With an identifier of 6 nucleotides, a maximum of 4096 unique combinations can be made (=4 exp 6). Preferably, the identifier contains a 2 base GC (or other defined short G/C-rich) anchor sequence at the 3' end to ensure equal binding affinity and amplification efficiency. Further it is preferred that the identifier does not contain two identical consecutive bases and it is further preferred that all identifiers used in a set of identifiers differ by at least two bases in order to ensure unequivocal sequence recognition. When multiple sample are used it is preferred that each sample can be identified using a specific set of identifiers. The identifier is generally located such that amplification of the ligated probes using the primer binding sequences will incorporate the identifier to the end that the resulting amplicon contains the identifier sequence. Typically this means that in the ligated probe, the identifier is located between the primer binding sites. In embodiments using two or more identifiers, for instance locus-allele combinations, the identifiers are also located between the primer binding sites. In certain embodiments, two identifiers are provided, one in each probe. One of the probes can be seen as a locus probe, i.e. directed to a specified locus and contains a locus specific identifier. The other probe can be an allele-specific probe, i.e. contain a allele specific nucleotide, preferably at its point of ligation. The allele specific probe may contain a allele specific identifier. In this way the presence or absence of a specific locus-allele combination is identified by the presence/absence of the combined identifiers. When testing for all allelic variation of a polymorphisms, only one locus probe is needed, combined with 4 allele specific probes. In certain embodiments, only the allele specific probe may comprise an identifier that comprises a locus specific identifier section and an allele specific identifier section, for instance in the form of a 5 bp locus identifier, followed by a 2 bp allele identifier.

Hybridisation

In certain embodiments, the probes are brought into hybridizing contact with the target sequence in the sample. The pairs of oligonucleotide probes are subsequently allowed to anneal to the, preferably adjacent, complementary parts of the target sequence in the sample. Methods and conditions for specific annealing of oligonucleotide probes to complementary target sequences are well known in the art (see e.g. in Sambrook and Russel (2001) "Molecular Cloning: A Laboratory Manual" (3rd edition), Cold Spring Harbor Laboratory, Cold Spring Harbor Laboratory Press).

Usually, after mixing of the oligonucleotide probes and target sequences the nucleic acids are denatured by incubation (generally at between 94 degrees Celsius and 96 degrees Celsius) for a short period of time (e.g. 30 seconds to 5 minutes) in a salt buffer. The sample containing the denatured probes and target sequences is then allowed to cool to an optimal hybridisation temperature for specific annealing of the probes and target sequences, which usually is about 5 degrees Celsius below the melting temperature of the hybrid between the complementary section (target section) of the probe and its complementary sequence (in the target sequence). In order to prevent aspecific or inefficient hybridisation of one of the two probes of a pair, or in a sample with multiple target sequences, it is preferred that, within one sample, the sections of the probes that are complementary to the target sequences are of a similar, preferably identical melting temperatures between the different target sequences present in the sample. Thus, the complementary sections of the first and second probes preferably differ less than 20, 15, 10, 5, or 2 degrees Celsius in melting temperature. This is facilitated by using complementary sections of the first and second probes with a similar length and/or similar G/C content, the complementary sections preferably differ less than 20, 15, 10, 5, or 2 nucleotides in length and their G/C contents differ by less than 30, 20, 15, 10, or 5%. Complementary as used herein means that a first nucleotide sequence is capable of specifically hybridising to second nucleotide sequence under normal stringency conditions. A nucleotide sequence that is considered complementary to another nucleotide sequence may contain a minor amount, i.e. preferably less than 20, 15, 10, 5 or 2%, of mismatches. Alternatively, it may be necessary to compensate for mismatches e.g. by incorporation of so-called universal nucleotides, such as for instance described in EP-A 974 672, incorporated herein by reference or by incorporation of certain modified nucleotides that are capable of compensating for mismatches for instance by increasing the melting temperature or increasing specificity such as LNAs. Since annealing of probes to target sequences is concentration dependent, annealing is preferably performed in a small volume, i.e. less than 25 microliter, preferably less than 10 microliter. Under these hybridisation conditions, annealing of probes to target sequences usually is fast and does not to proceed for more than 5, 10 or 15 minutes, although longer annealing time may be used as long as the hybridisation temperature is maintained to avoid aspecific annealing. Longer annealing times are more important/required for quantitative applications which rely on complete target occupation by ligation probes in order to allow monitoring or relative amounts of target sequences between samples.

In certain embodiments, of the invention, excellent results have been obtained by prolonged hybridisation times such as overnight hybridisation or by repeated hybridisation, such as 10 cycles of 1 hour. Prolonged hybridisation times can be advantageous in these assays as the difference in signal due to different hybridisation efficiencies is reduced and it is considered desirable to achieve complete hybridisation and ligation of all probes for which a target sequence is present. Excellent results have been obtained by a combined hybridisation-ligation step using a thermostable ligase described herein. In this embodiment the hybridisation-ligation was performed by allowing the probes to hybridise during 1 hour in the presence of a thermostable ligase, followed by a denaturation step. Repeating these steps for at least 2 times provided good results. Repeating these steps 10 times provided excellent results. To avoid evaporation during denaturation and annealing, the walls and lids of the reaction chambers (i.e. tubes or microtitre wells) may also be heated to at least the same temperature as the reaction mixture which is commonly achieved by the use of commercial DNA amplification equipment or by providing a mineral oil overlay. In preferred oligonucleotide probes the length of the target-complementary section is preferably at least 15, 18 or 20 nucleotides and preferably not more than 30, 40, or 50 nucleotides and the probes preferably have a melting temperature from the target section of at least 50 degrees Celsius, 55 degrees Celsius or 60 degrees Celsius.

Ligation

The respective 5'-phosphorylated and 3'-hydroxylated ends of a pair of first and second oligonucleotide probes or of the circularizable probe of which the target specific sections are annealed essentially adjacent to each other to the complementary parts on a target sequence are connected to form a covalent bond by any suitable means known in the art. The ends of the probes may be enzymatically connected into a phosphodiester bond by a ligase, preferably a DNA ligase. DNA ligases are enzymes capable of catalysing the formation of a phosphodiester bond between (the ends of) two polynucleotide strands bound at adjacent sites on a complementary strand. DNA ligases usually require ATP (EC 6.5.1.1) or NAD (EC 6.5.1.2) as a cofactor to seal nicks in double stranded DNA.

Suitable DNA ligase for use in the present invention are T4 DNA ligase, *E. coli* DNA ligase or preferably a thermostable ligase like e.g. *Thermus aquaticus* (Taq) ligase, *Thermus thermophilus* DNA ligase, or *Pyrococcus* DNA ligase.

Alternatively, chemical ligation of suitably modified polynucleotide ends may be used to ligate two oligonucleotide probes annealed at adjacent sites on the complementary parts of a target sequence. Exemplary reactive groups on modified polynucleotide ends include, but are not limited to, phosphorothioate and tosylate or iodide, esters and hydrazide, RC(O)S, RCH2S and [alpha]-haloacyl, thiophosphoryl and bromoacetamide groups, and S-pivaloyloxymethyl-4-thiothymidine.

Chemical ligation agents include, without limitation, activating, condensing, and reducing agents, such as carbodiimide, cyanogen bromide (BrCN), N-cyanoimidazole, imidazole, 1-methylimidazole/carbodiimide/cystamine, dithiothreitol (DTT) and ultraviolet light. Autoligation, i.e., spontaneous ligation in the absence of a ligating agent, is also within the scope of the invention. Detailed protocols for chemical ligation methods and descriptions of appropriate reactive groups can be found, among other places, in Xu et al., Nucleic Acid Res., 27: 875-81 (1999) Gryaznov and Letsinger, Nucleic Acid Res. 21: 1403-08 (1993) Gryaznov et al., Nucleic Acid Res. 22: 2366-69 (1994); Kanaya and Yanagawa, Biochemistry 25: 7423-30 (1986); Luebke and Dervan, Nucleic Acids Res. 20: 3005-09 (1992); Sievers and von Kiedrowski, Nature 369: 221-24 (1994); Liu and Taylor, Nucleic Acids Res. 26: 3300-04 (1999); Wang and Kool, Nucleic Acids Res. 22: 2326-33 (1994); Purmal et al., Nucleic Acids Res. 20: 3713-19 (1992); Ashley and Kushlan, Biochemistry 30: 2927-33 (1991); Chu and Orgel, Nucleic Acids Res. 16: 3671-91 (1988); Sokolova et al., FEBS Letters 232: 153-55 (1988); Naylor and Gilham, Biochemistry 5:2722-28 (1966); and U.S. Pat. No. 5,476,930.

Both chemical and enzymatic ligation occur much more efficient on perfectly matched probe-target sequence complexes compared to complexes in which one or both of the probes form a mismatch with the target sequence at, or close to the ligation site (Wu and Wallace, 1989, Gene 76: 245-254; Xu and Kool, supra). In order to increase the ligation specificity, i.e. the relative ligation efficiencies of perfectly matched oligonucleotides compared to mismatched oligonucleotides, the ligation is preferably performed at elevated temperatures. Thus, in certain embodiments, of the invention, a DNA ligase is employed that remains active at 50-65 degrees Celsius for prolonged times, but which is easily inactivated at higher temperatures, e.g. used in the denaturation step during a PCR, usually 90-100 degrees Celsius. One such DNA ligase is a NAD requiring DNA ligase from a Gram-positive bacterium (strain MRCH 065) as known from WO01/61033. This ligase is referred to as "Ligase 65" and is commercially available from MRC Holland, Amsterdam. In certain embodiments, a Taq Ligase is used. In certain embodiments, the ligase is inactivated-after ligating the first and second probes. In certain embodiments, the connected probe is denatured from the target sequence.

Gap Ligation

In an alternative embodiment, for instance directed to the identification of indels, the respective ends of the target complementary sections of the first and second probe may be annealed such that a gap is left. In certain embodiments, the first and second parts of the target nucleotide sequence are not located adjacent. In other words, the first and second target specific sections of the first and second probe are not hybridized to first and second parts of the target nucleotide sequence that are located adjacent. This is fundamentally different from other varieties of this technology such as disclosed inter alia in EP 185494, U.S. Pat. No. 5,521,065, U.S. Pat. No. 5,692,223 and WO 03054311. This gap can be filled with a suitable (third) (oligo)nucleotide and ligated. Such methods are known in the art as 'gap ligation' and are disclosed inter alia in WO 00/77260; U.S. Pat. No. 5,185,243; EP439182; EP320308; WO90/01069. Another possibility to fill this gap is by extension of one end of the probe using a polymerase and a ligase in combination with single or multiple nucleotides, optionally preselected from A, T, C, or G, or di-, tri- or other small oligonucleotides. In case the target sequence is RNA, yet another possibility to fill the gap is by extension of one end of the probe using reverse transcriptase and a ligase in combination with single or multiple nucleotides, optionally preselected from A, T, C, or G, or di, tri- or other small oligonucleotides.

Gap ligation may find application in both the detection of single SNPs/indels or multiple SNPs (haplotyping) that are closely located.

Amplification

In the method of the invention, the connected probes are amplified to produce an amplified sample comprising amplified (detectable) connected probes (amplicons) that are representations of the target nucleotide sequence by any suitable nucleic acid amplification method known in the art. Nucleic acid amplification methods usually employ one or two primers, dNTPs, and a (DNA) polymerase. A preferred method for amplification is PCR. "PCR" or "Polymerase Chain Reaction" is a rapid procedure for in vitro enzymatic amplification of a specific DNA segment. The DNA to be amplified is denatured by heating the sample. In the presence of DNA polymerase and excess deoxynucleotide triphosphates, oligonucleotides that hybridize specifically to the target sequence prime new DNA synthesis. It is preferred that the polymerase is a DNA polymerase that does not express strand displacement activity or at least not significantly. Examples thereof are Amplitaq and Amplitaq Gold (supplier Perkin Elmer) and Accuprime (Invitrogen). One round of synthesis results in new strands of determinate length, which, like the parental strands, can hybridise to the primers upon denaturation and annealing. The second cycle of denaturation, annealing and synthesis produces two single-stranded products—that together compose a discrete double-stranded product, exactly the length between the primer ends. This discrete product accumulates exponentially with each successive round of amplification. Over the course of about 20 to 30 cycles, many million-fold amplification of the discrete fragment can be achieved. PCR protocols are well known in the art, and are described in standard laboratory textbooks, e.g. Ausubel et al., Current Protocols in Molecular Biology, John Wiley & Sons, Inc. (1995). Suitable conditions for the application of PCR in the method of the invention are described in EP-A 0 534 858 and Vos et al. (1995; Nucleic Acids Res. 23: 4407-4414), where multiple DNA fragments between 70 and 700 nucleotides and containing identical primer-binding sequences are amplified with near equal efficiency using one primer pair. In certain embodiments, the polymerase is inactivated after amplification. Other multiplex and/or isothermal amplification methods that may be applied include e.g. rolling circle amplification (RCA), ligase chain reaction (LCR), self-sustained sequence replication (3SR), Q-B-replicase mediated RNA amplification, or strand displacement amplification (SDA). In some instances, this may require a different design of the probes and primers without departing from the gist of the invention.

Primers

The connected probe is amplified using a pair of primers corresponding to the primer-binding sites. In certain embodiments, the pair of primers contains only one primer and the amplification is linear rather than exponential. In certain embodiments, the pair comprises a first primer that is capable annealing to the first primer-binding section and capable of initiating amplification or elongation. In certain embodiments, the pair further comprises a second primer that is capable annealing to the second primer-binding section and capable of initiating amplification or elongation. In certain embodiments, the second primer has the same sequence as the second primer binding site in the probe. In a preferred embodiment, at least one of the primers or the same pair of primers is used for the amplification of two or more different connected probes in a sample, preferably for the amplification of all connected probes in a sample. Such a primer is sometimes referred to as a universal primer as these primers are capable of priming the amplification of all connected probes containing the corresponding universal primer binding site and consequently of all ligated probes containing the universal primer binding site. The different primers that are used in the amplification in step (i) are preferably essentially equal in annealing and priming efficiency. Thus, the primers in a sample preferably differ less than 20, 15, 10, 5, or 2 degrees Celsius in melting temperature. This can be achieved as outlined herein for the target-specific sections of the oligonucleotide probes. Unlike the sequence of the target-specific sections, the sequence of the primers is not dictated by the target sequence. Primer sequences may therefore conveniently be designed by assembling the sequence from tetramers of nucleotides wherein each tetramer contains one A, T, C and G or by other ways that ensure that the G/C content and melting temperature of the primers are identical or very similar. The length of the primers (and corresponding primer-binding sites in the tag section of the second probe) is preferably at least 12, 15 or 17 nucleotides and preferably not more than 25, 30, 40 nucleotides.

In a certain embodiment, at least two of the second oligonucleotide probes that are complementary to at least two different target sequences in a sample each comprise a tag section that comprises a primer-binding section that is complementary to a single primer sequence.

In certain embodiments, to ensure similar priming efficiency compared to other primers harbouring the same anchor sequence, the primer may comprise a 3' anchoring sequence, preferably a 2 bp anchoring sequence, preferably a GC anchoring sequence. Typically, the corresponding primer binding sequence will also harbour the complement thereof.

Thus, preferably at least one of the first and second primer in a primer pair is used for the amplification of connected probes corresponding to at least two different target sequences in a sample, more preferably for the amplification of connected probes corresponding to all target sequences in a sample. Preferably only a single first primer is used and in some embodiments only a single first and a single second primer is used for amplification of all connected probes.

Using common primers for amplification of multiple different fragments usually is advantageous for the efficiency of the amplification step. The connected probes obtained from the ligation of the adjacently annealed probe sections are amplified, using a primer pair, preferably consisting of a pair of primers for each of the connected probes in the sample. The primer pair comprises primers that are complementary to primer-binding sequences that are present in the connected probe. A primer pair usually comprises a first and at least a second primer, but may consist of only a single primer that primes in both directions. Excellent results have been obtained using primers that are known in the art as AFLP-primers such as described inter alia in EP534858 and in Vos et al., Nucleic Acid Research, 1995, vol. 23, 4407-44014 and discussed in more detail herein below.

Selective Primers

In certain embodiments, one or more of the primers used in the amplification step of the present invention is a selective primer. A selective primer is defined herein as a primer that, in addition to its universal sequence which is complementary to a primer binding site in the probe, contains a region that comprises so-called "selective nucleotides". The region containing the selective nucleotides is located at the 3'-end of the universal primer. The principle of selective nucleotides is disclosed inter alia in EP534858 and in Vos et al., Nucleic Acid Research, 1995, vol. 23, 4407-44014 albeit in a different context, i.e. DNA fingerprinting. The selective nucleotides are complementary to the nucleotides in the (ligated) probes that are located adjacent to the primer binding sequence. The selective nucleotides generally do not form part of the region in the (ligated) probes that is depicted as the primer binding sequence. Primers containing selective nucleotide are denoted as +N primers, in which N stands for the number of selective nucleotides present at the 3'-end of the primer. N is preferably selected from amongst A, C, T or G.

Amplicons

Figure 2:
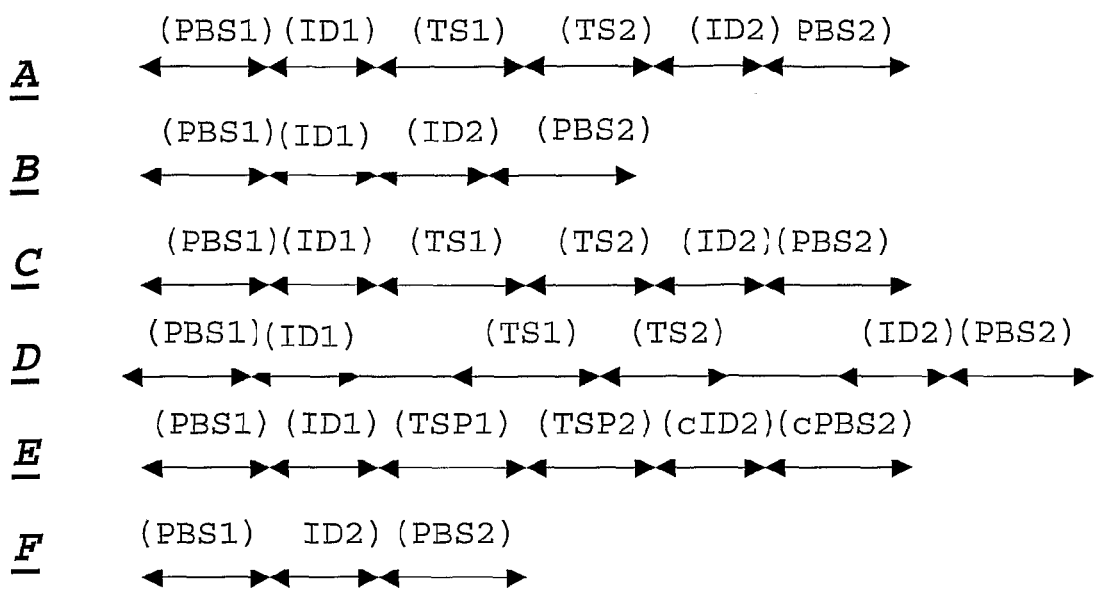
FIG. 2 illustrates the principal structure of the ligated probes/amplicons after ligation/amplification for each of the probes types of FIG. 1A through 1F
Figure 3:
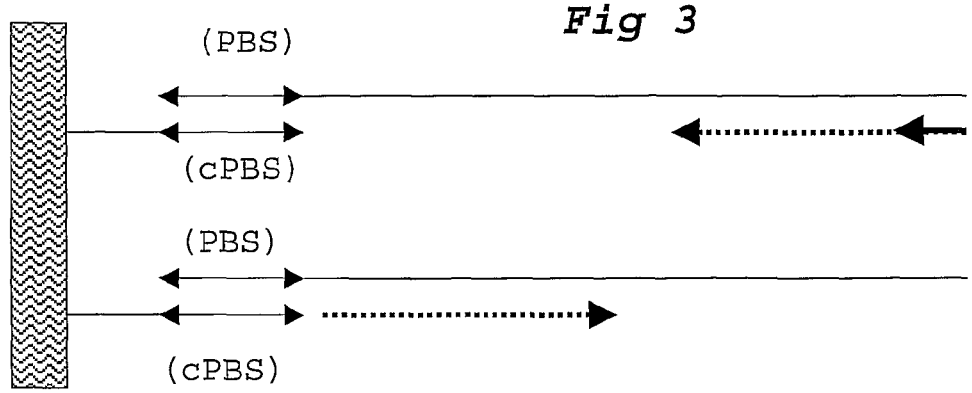
FIG. 3 illustrates schematically the high throughput sequencing step of the present invention whereby the ligated probes/amplicons are bound to a surface (a bead in the case of the emulsion PCR followed by pyrosequencing in the case of the 454 technology or the surface of the flow cell). The surface is provided with a sequence (cPBS) that is capable of annealing to one or both primer binding sequences PBS. After hybridisation of the ligated probe/amplicon to the surface, the hybridised sequence can be amplified to either load the bead with amplified sequences or to generate clusters of amplified sequences on the surface of the flow cell. Subsequently, these sequence can be determined using the described high throughput sequencing technologies. The sequence can be determined uni- or bidirectional, by adding sequencing primers, nucleotides and enzymes.
Figure 4:
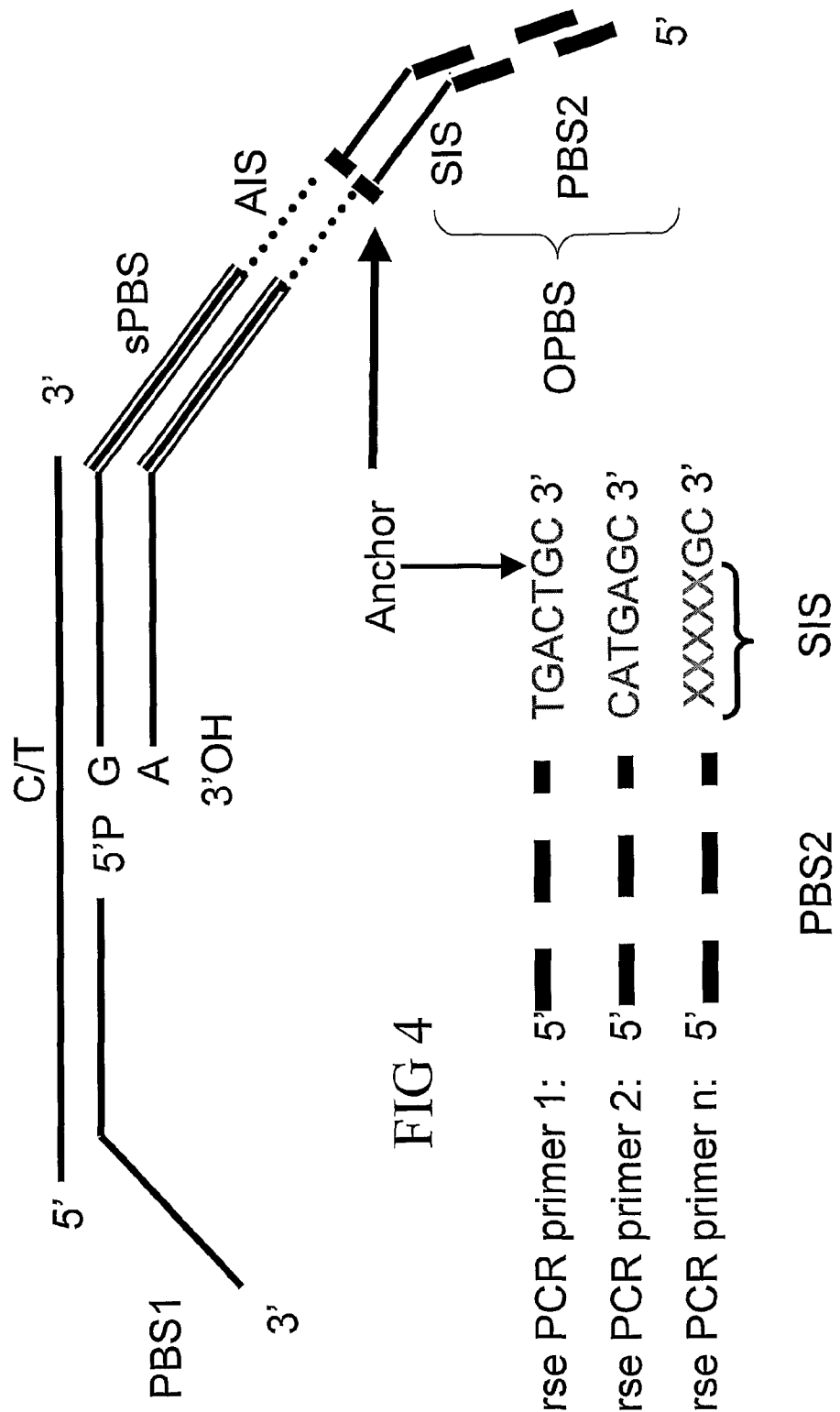
FIG. 4 to 15 illustrates a set of degenerate ligation probes (i.e. for an allele 'A' and 'G') that comprise, in addition to, or as replacement of the elements depicted in FIG. 1 such as the target sections (TS1, TS2 etc.), a separate primer binding site for the sequencing step (sPBS) and a (reverse) PCR primer binding site (PBS2). The sample specific reverse) primer binding site (OPBS) is degenerated by the introduction of a variable part that functions as a sample identifier (SIS). Each sample can be selectively amplified using sample specific primers (SSP), shown here for sample 1, 2 until n. The use of multiple, degenerated reverse primers are more economical and can be used for multiple assays. Pooled samples can be amplified using a correspondingly degenerated set of primers. Equal primer binding and amplification efficiency of all alleles or samples can be provided by the use of GC anchor sequences. The probes may further contain an optional C located at the 5' end of the primer binding site, with a corresponding C located at the 3' end of the (reverse) primer (SSP). The probes may further contain an allele identifier (AIS) for each allele to be investigated. The allele and sample identifiers are preferably from 3 to 5 bp, with preferably no two identical consecutive bases (homopolymers). Preferably the identifier differ by at least two bases.
Figure 5:
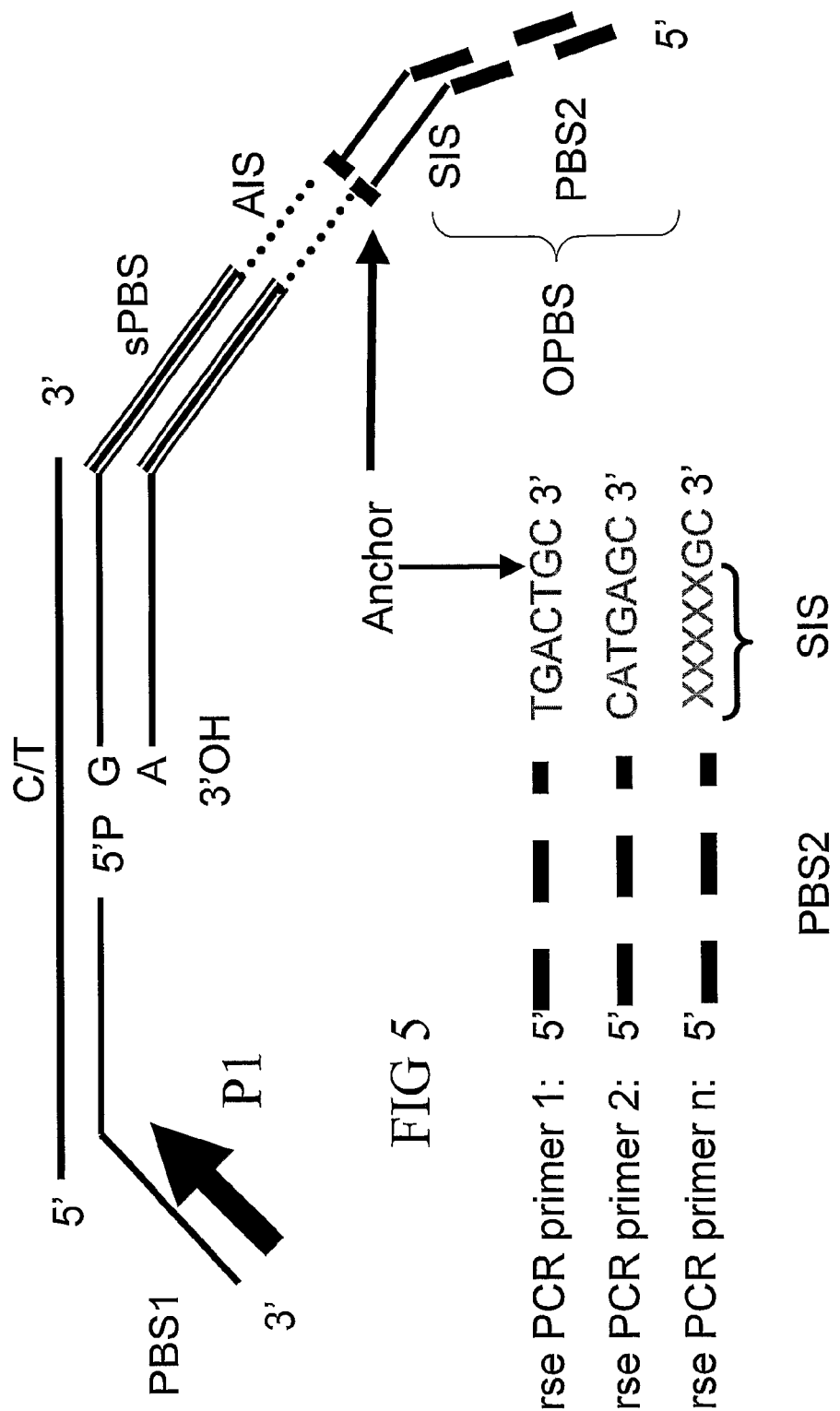
Figure 6:
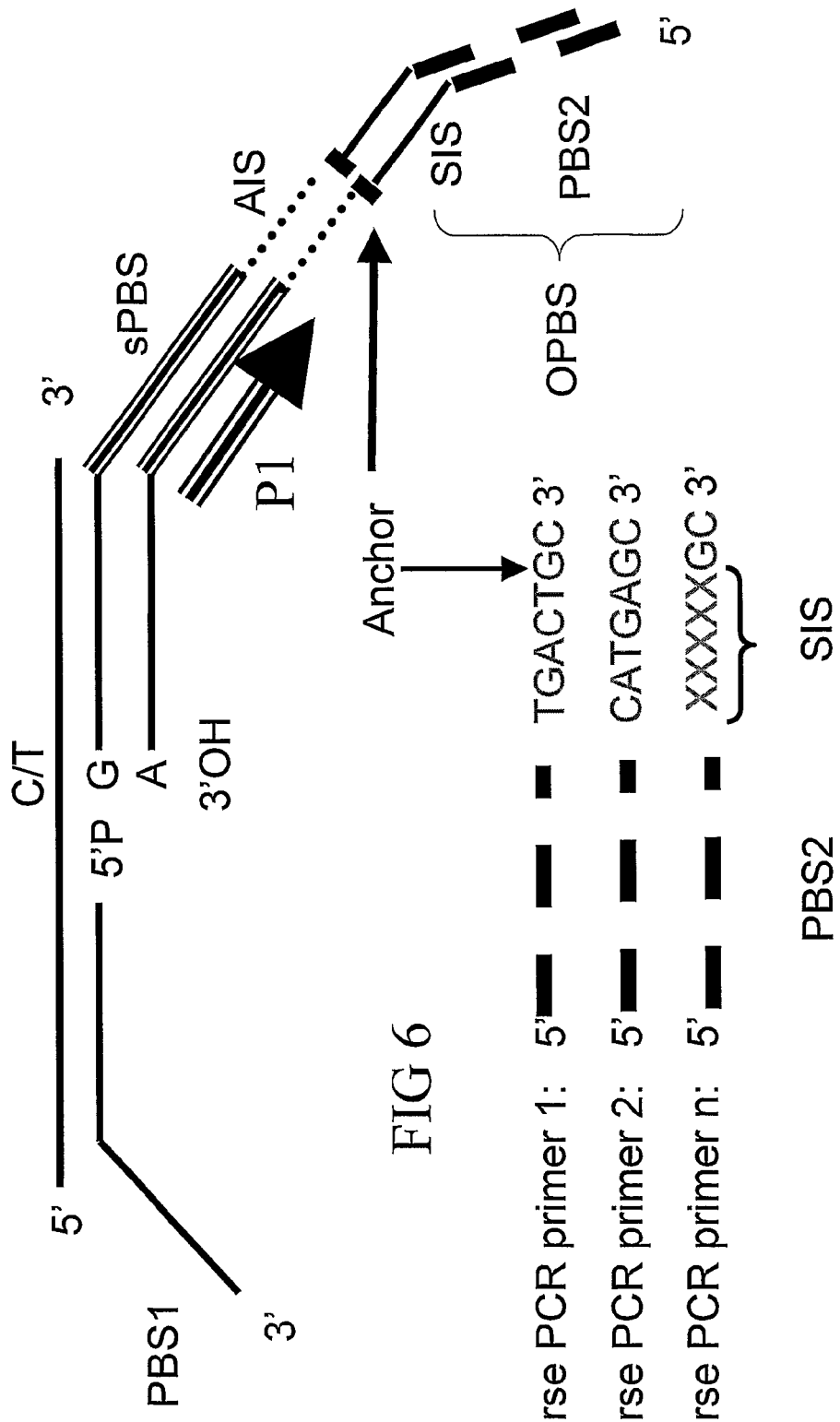
Figure 7:
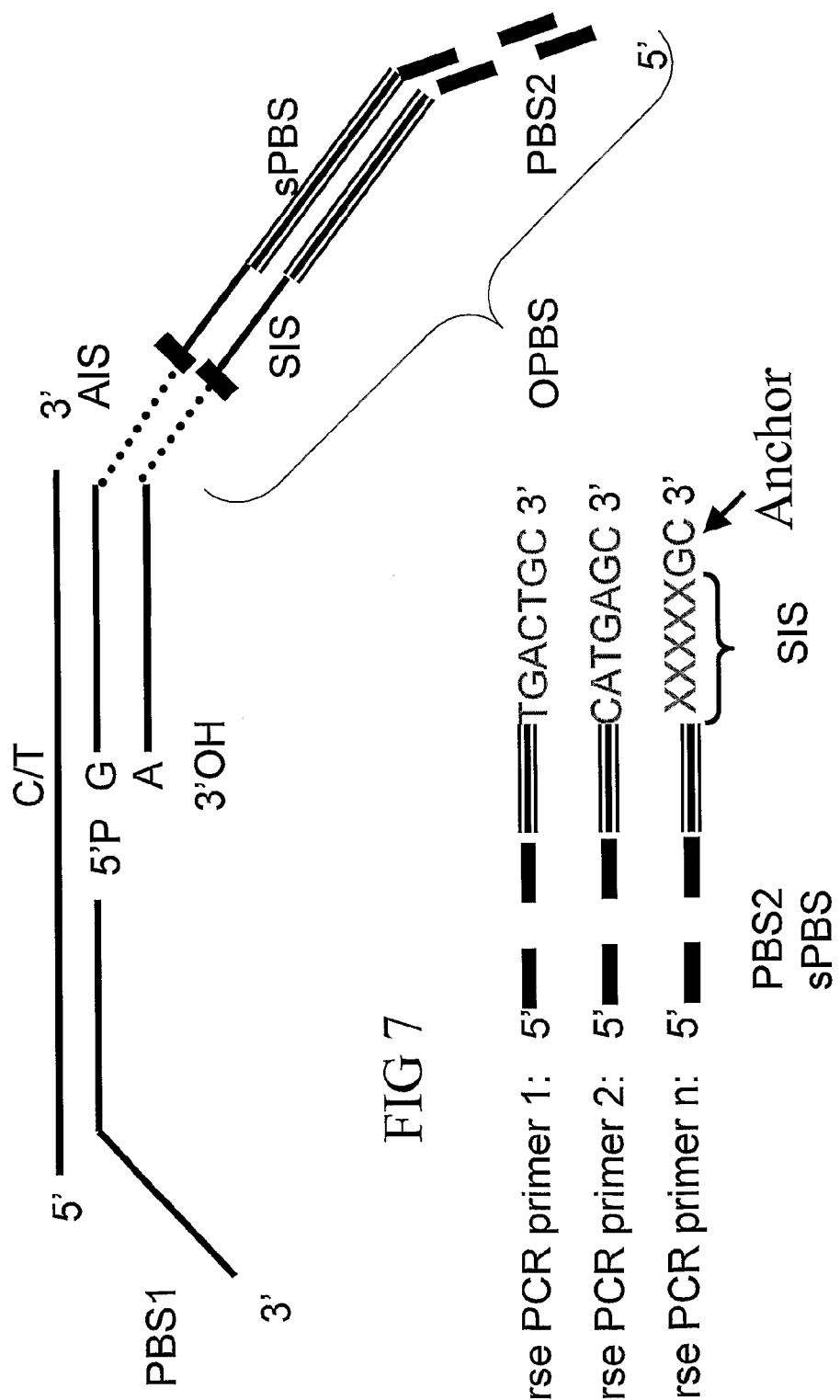
Figure 8:
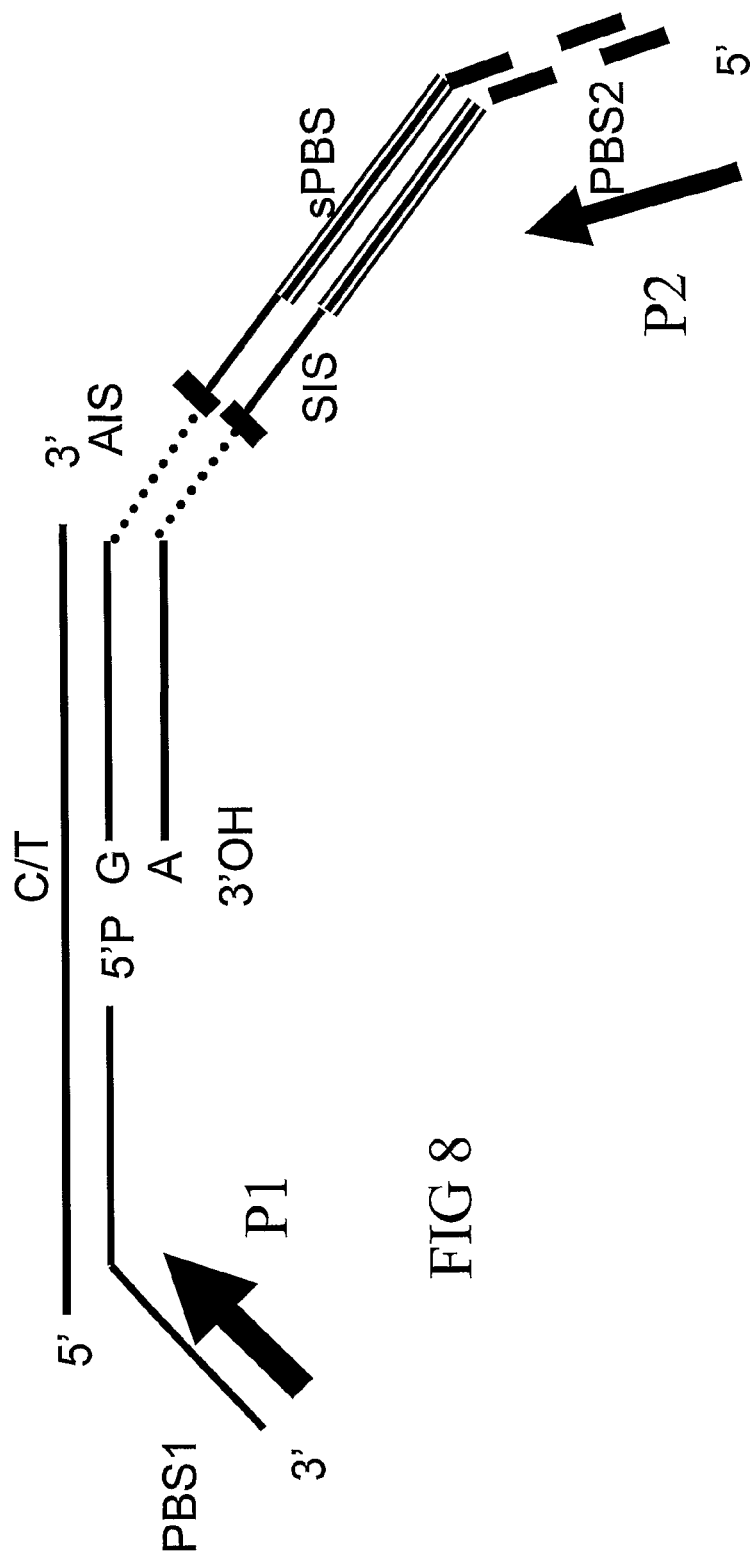
Figure 9:
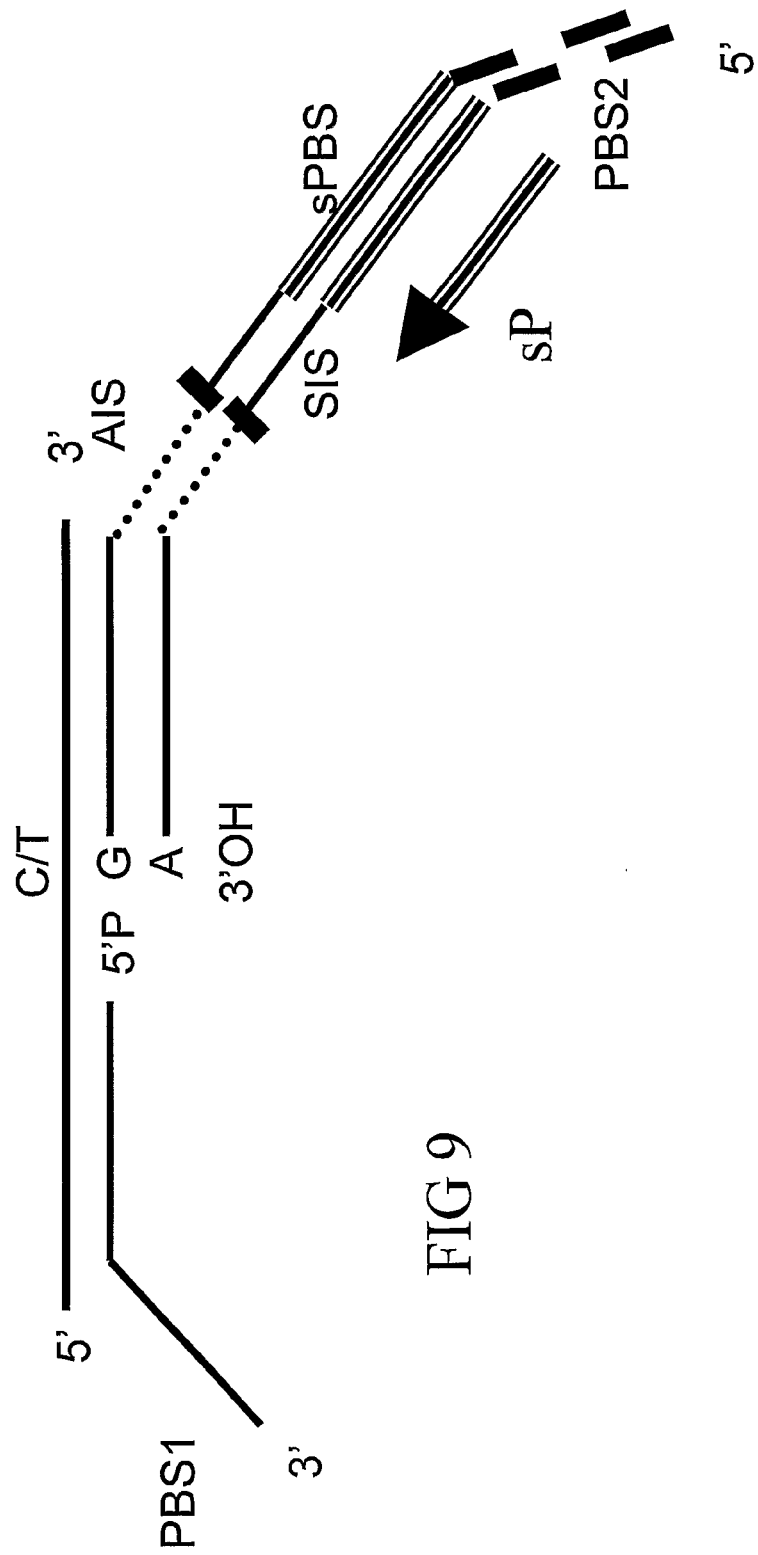
Figure 10:
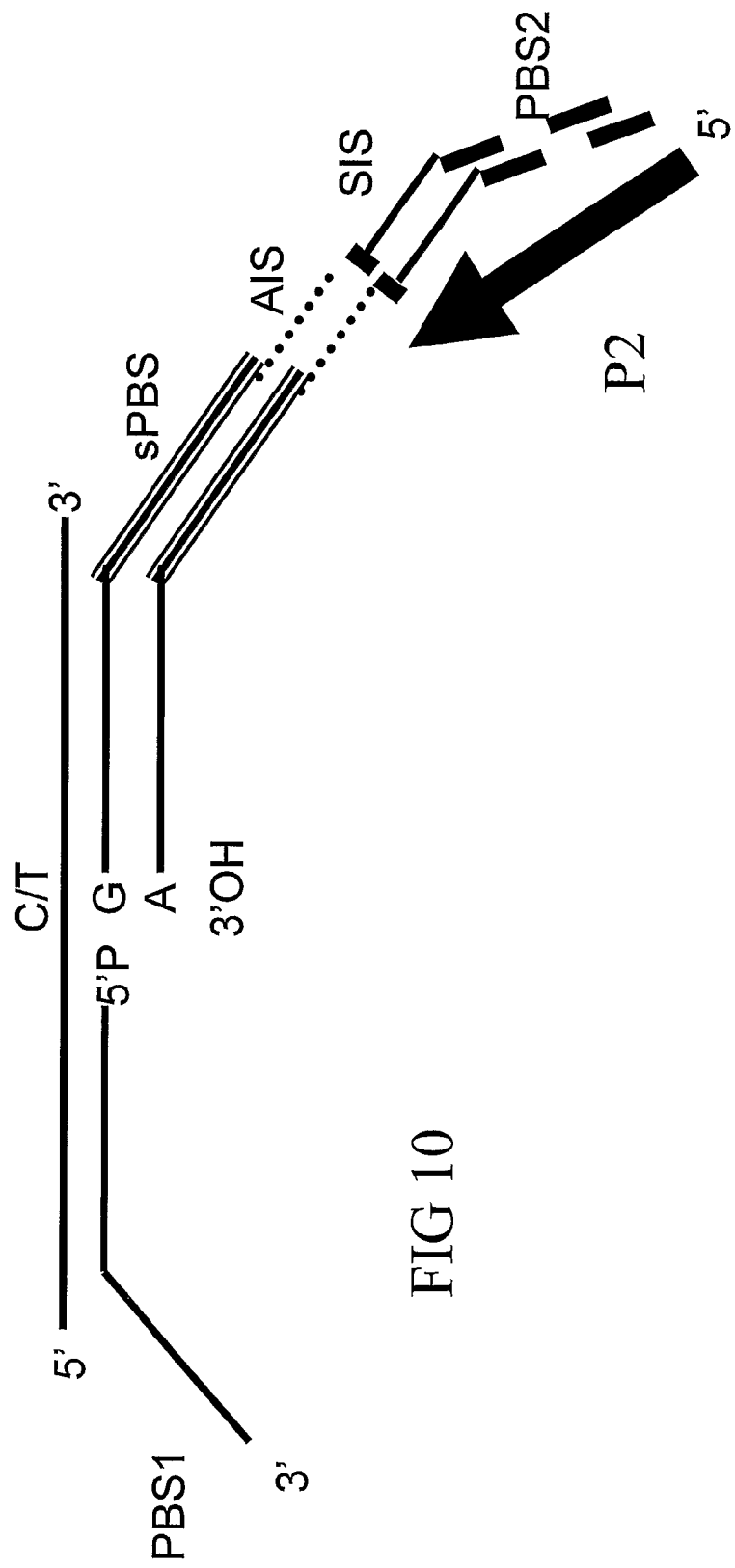
Figure 11:
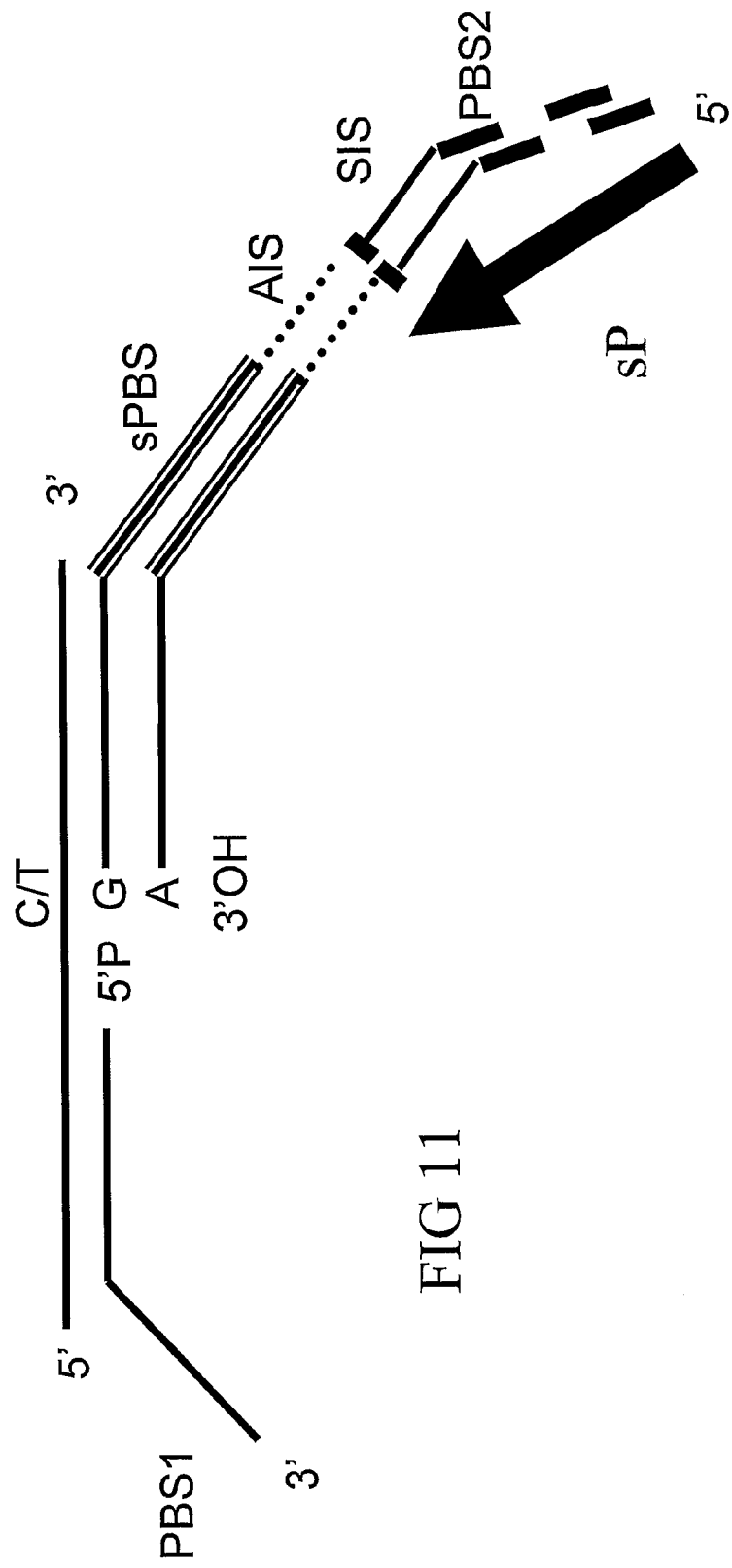
Figure 12:
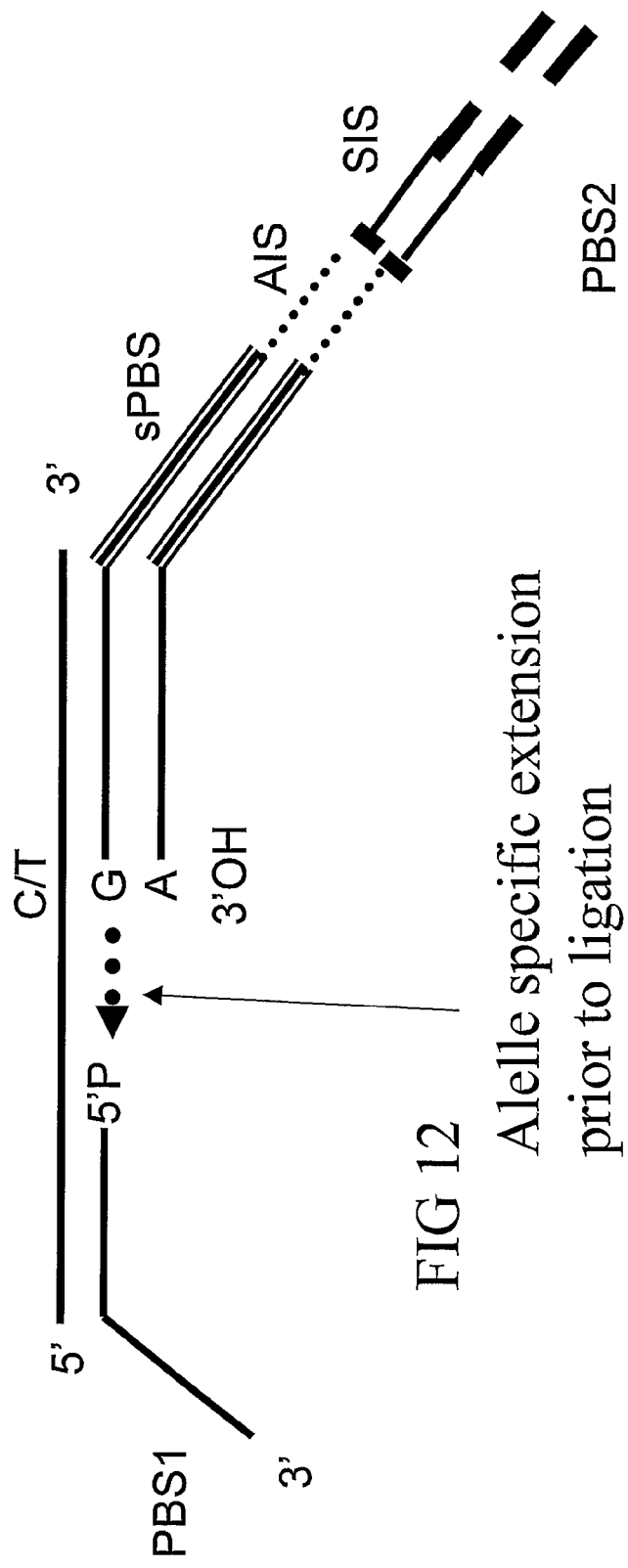
Figure 13:
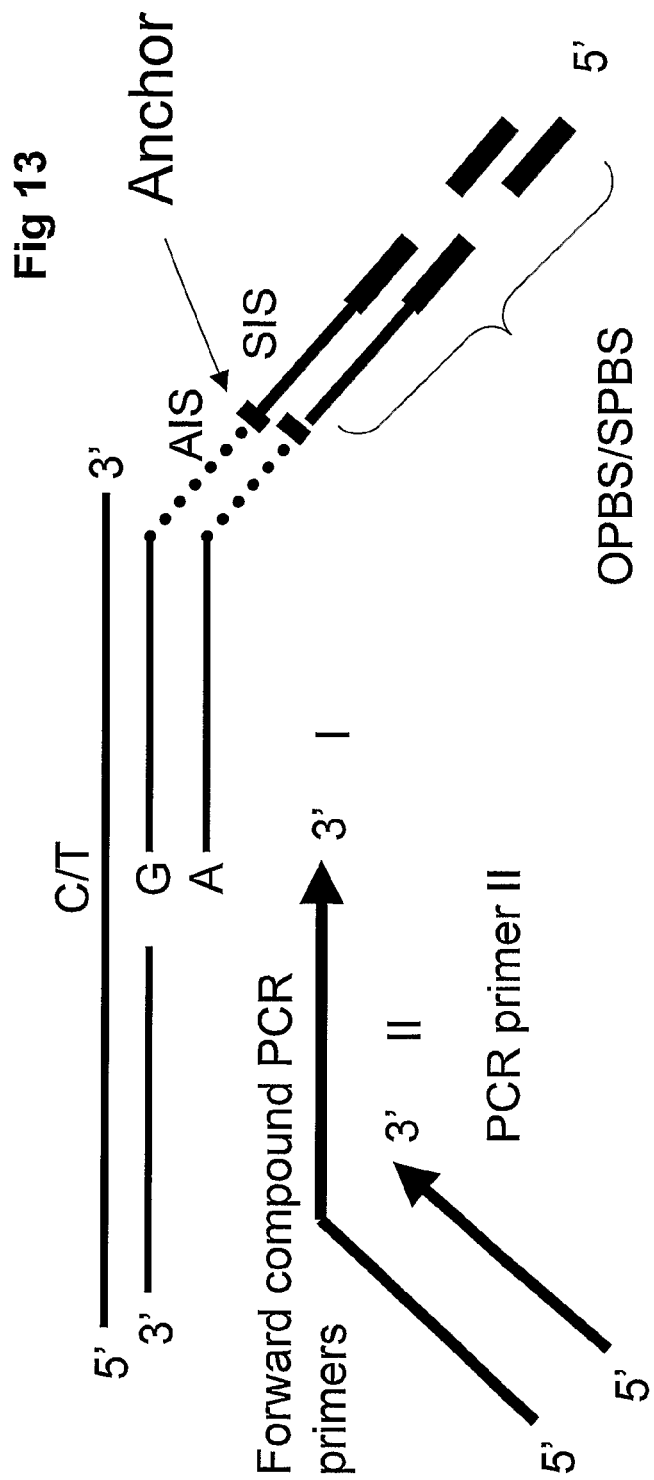
Figure 14:
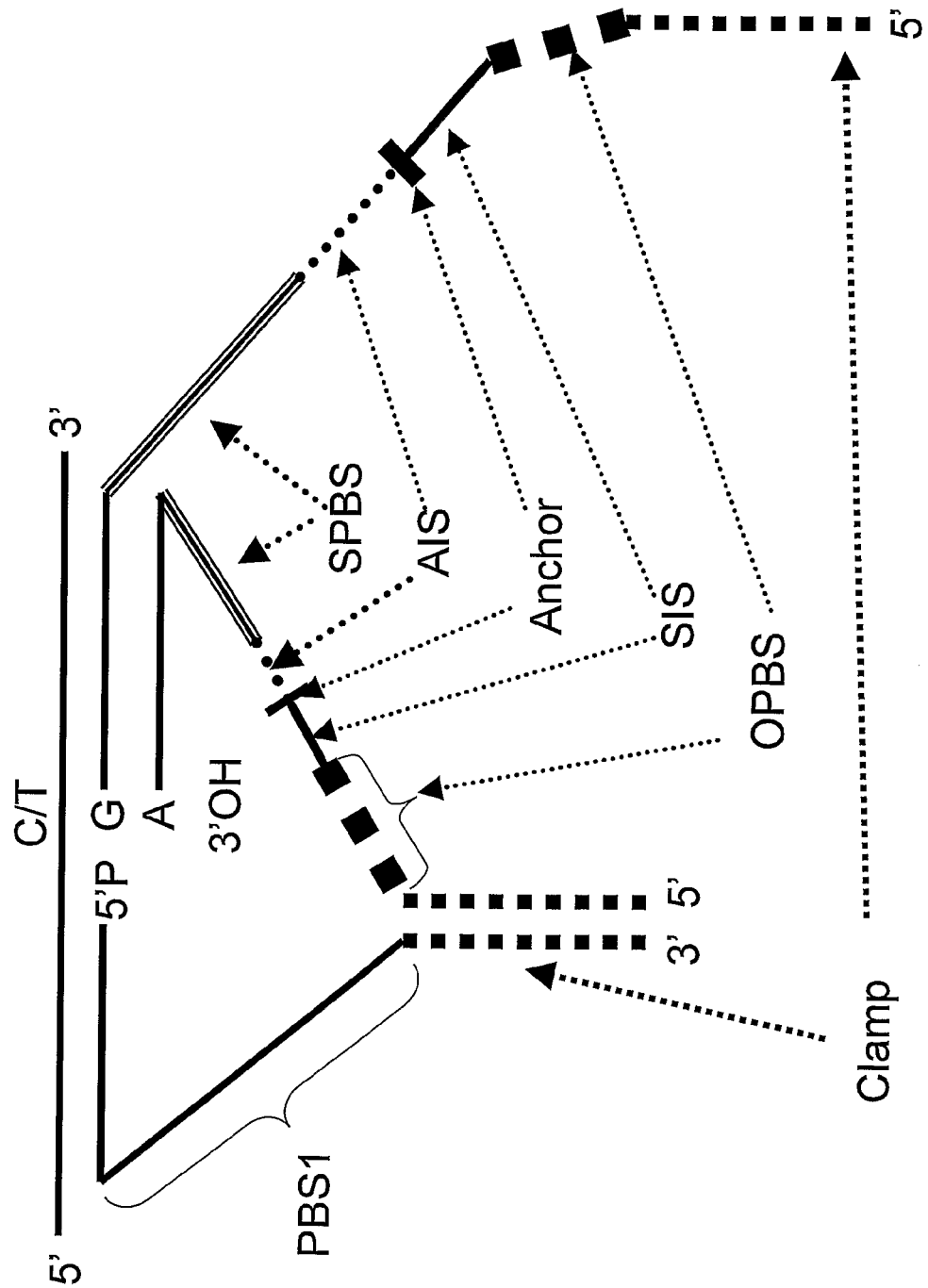
Figure 15:
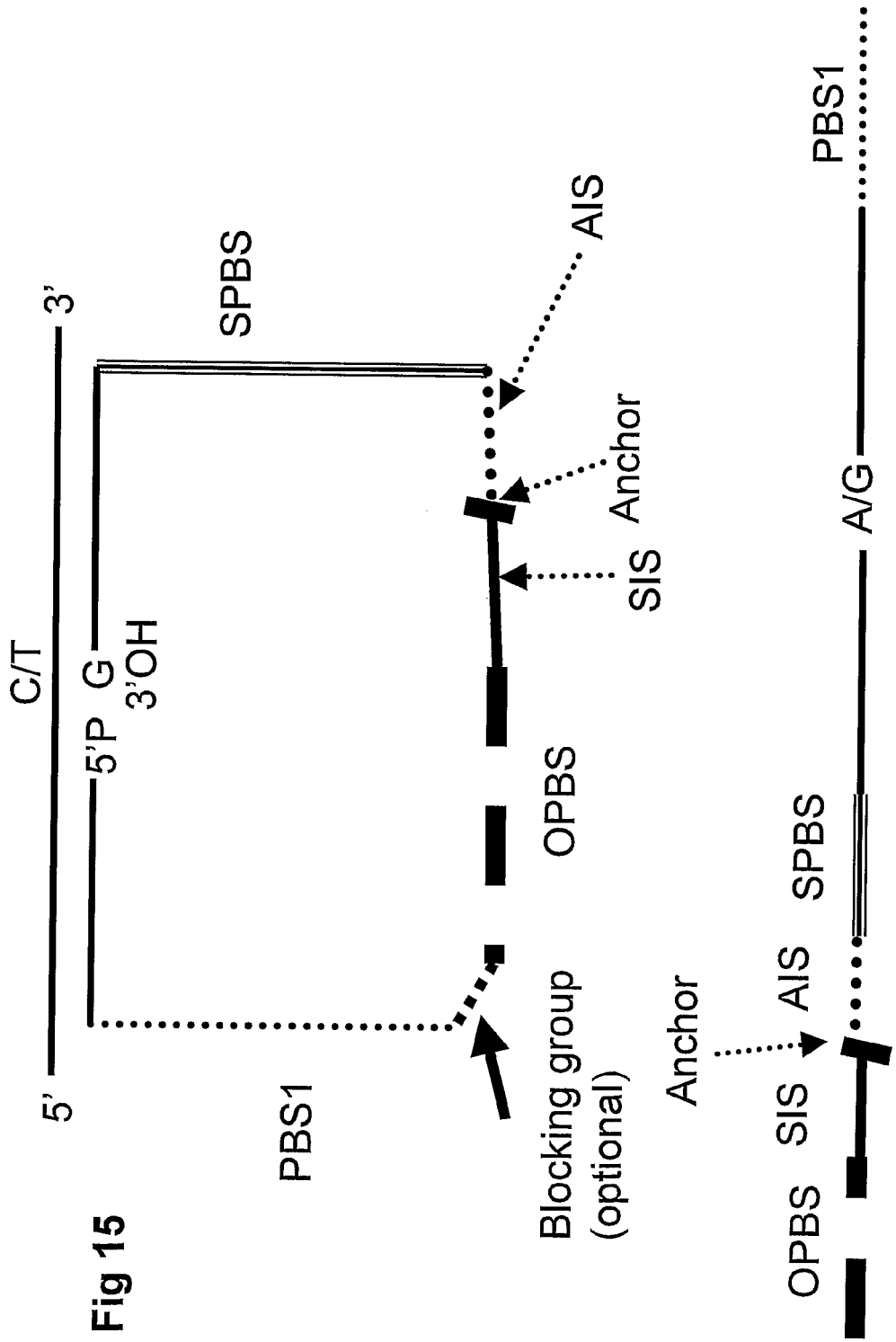

The term 'amplicon' as used herein refers to the product of the amplification step of the connected probes. The term 'amplicon' as used herein thus refers to an amplified connected probe. After the ligation step wherein the two target specific sections are connected by mean of a ligase, the connected or ligated probe is combined with one or more primers and a polymerase and amplified to produce amplicons. The ligated probe, the primers, the polymerase and/or other parameters and variables are such that the amplification results in amplified linear representations of the connected probe. Preferably an amplicon is a monomeric representation of the amplified connected probe. In certain embodiments, the amplicon comprises and preferably consists of the nucleotides of the first and optional second primer and the identifier(s) that is (are) located in-between. The various embodiments of the present invention will provide further detail in this respect (FIG. 2).

High Throughput Sequencing

High-throughput sequencing or screening, often abbreviated as HTS, is a method for scientific experimentation especially relevant to the fields of biology and chemistry. Through a combination of modern robotics and other specialised laboratory hardware, it allows a researcher to effectively screen large amounts of samples simultaneously.

It is preferred that the sequencing is performed using high-throughput sequencing methods, such as the methods disclosed in WO 03/004690, WO 03/054142, WO 2004/069849, WO 2004/070005, WO 2004/070007, and WO 2005/003375 (all in the name of 454 Life Sciences), by Seo et al. (2004) Proc. Natl. Acad. Sci. USA 101:5488-93, and technologies of Helios, Solexa, US Genomics, etcetera, which are herein incorporated by reference.

454 Technology

In certain embodiments, it is preferred that sequencing is performed using the apparatus and/or method disclosed in WO 03/004690, WO 03/054142, WO 2004/069849, WO 2004/070005, WO 2004/070007, and WO 2005/003375 (all in the name of 454 Life Sciences), which are herein incorporated by reference. The technology described allows sequencing of 40 million bases in a single run and is 100 times faster and cheaper than competing technology. The sequencing technology roughly consists of 5 steps: 1) fragmentation of DNA and ligation of specific adaptors to create a library of single-stranded DNA (ssDNA); 2) annealing of ssDNA to beads, emulsification of the beads in water-in-oil microreactors and performing emulsion PCR to amplify the individual ssDNA molecules on beads; 3) selection of/enrichment for beads containing amplified ssDNA molecules on their surface 4) deposition of DNA carrying beads in a PicoTiter™ Plate; and 5) simultaneous sequencing in 100,000 wells by generation of a pyrophosphate light signal. The method will be explained in more detail below.

In a preferred embodiment, the sequencing comprises the steps of:
(a) annealing adapted fragments to beads, each bead being annealed with a single adapted fragment;
(b) emulsifying the beads in water-in-oil microreactors, each water-in-oil microreactor comprising a single bead;
(c) loading the beads in wells, each well comprising a single bead; and generating a pyrophosphate signal.

In the first step (a), sequencing adaptors are ligated to fragments within the combination library. Said sequencing adaptor includes at least a "key" region for annealing to a bead, a sequencing primer region and a PCR primer region. Thus, adapted fragments are obtained. In a first step, adapted fragments are annealed to beads, each bead annealing with a single adapted fragment. To the pool of adapted fragments, beads are added in excess as to ensure annealing of one single adapted fragment per bead for the majority of the beads (Poisson distribution).

In a next step, the beads are emulsified in water-in-oil microreactors, each water-in-oil microreactor comprising a single bead. PCR reagents are present in the water-in-oil microreactors allowing a PCR reaction to take place within the microreactors. Subsequently, the microreactors are broken, and the beads comprising DNA (DNA positive beads) are enriched.

In a following step, the beads are loaded in wells, each well comprising a single bead. The wells are preferably part of a PicoTiter™ Plate allowing for simultaneous sequencing of a large amount of fragments.

After addition of enzyme-carrying beads, the sequence of the fragments is determined using pyrosequencing. In successive steps, the PicoTiter™ plate and the beads as well as the enzyme beads therein are subjected to different deoxyribonucleotides in the presence of conventional sequencing reagents, and upon incorporation of a deoxyribonucleotide a light signal is generated which is recorded. Incorporation of the correct nucleotide will generate a pyrosequencing signal which can be detected.

Pyrosequencing itself is known in the art and described inter alia on www.biotagebio.com; www.pyrosequencing.com. The technology is further applied in e.g. WO 03/004690, WO 03/054142, WO 2004/069849, WO 2004/

070005, WO 2004/070007, and WO 2005/003375 (all in the name of 454 Life Sciences), which are herein incorporated by reference.

In the present invention, the beads are preferably equipped with primer (binding) sequences and/or clamp sections or parts thereof that are capable of binding the amplicons or the ligated probes, as the case may be. In other embodiments, the probes or the primers used in the amplification are equipped with sequences that allow binding of the amplicons or the ligated probes to the beads in order to allow subsequent emulsion polymerisation followed by sequencing. The sequenced amplicons of ligated probes will reveal the identity of the identifier and thus of the presence or absence of the target sequence in the sample.

Solexa Technologies

One of the methods for high throughput sequencing is available from Solexa, United Kingdom (www.solexa.co.uk) and described inter alia in WO0006770, WO0027521, WO0058507, WO0123610, WO0157248, WO0157249, WO02061127, WO03016565, WO03048387, WO2004018497, WO2004018493, WO2004050915, WO2004076692, WO2005021786, WO2005047301, WO2005065814, WO2005068656, WO2005078130. In essence, the method start with adapter-ligated fragments of genomic DNA. The adapter ligated DNA is randomly attached to a dense lawn of primers that are attached to a solid surface, typically in a flow cell. The other end of the adapter ligated fragment hybridizes to a complementary primer on the surface. The primers are extended in the presence of nucleotides and polymerases in a so-called solid-phase bridge amplification to provide double stranded fragments. Denaturation and repetition of the solid-phase bridge amplification results in dense clusters of amplified fragments distributed over the surface. The sequencing is initiated by adding four differently labelled reversible terminator nucleotides, primers and polymerase to the flow cell. After the first round of primer extension, the labels are detected, the identity of the first incorporated bases is recorded and the blocked 3' terminus and the fluorophore are removed from the incorporated base. Then the identity of the second base is determined in the same way and so sequencing continues.

In the present invention, the ligated probes or the amplicons are bound to the surface via the primer binding sequence, the primer sequence or in some embodiments, the clamp section or a combination thereof. The sequence is determined as outlined, including the identifier sequence and the associated target sequence and its presence or absence is identified.

In alternative embodiments directed to the sequencing methods described herein, the probes or the primers used in the amplification may contain specific sections (as alternative to the herein described primer or primer binding sequences) that are used in the subsequent sequencing step to bind the ligated probes/amplicons to the surface. These are generally depicted as the key region.

Throughout this specification, figures and the appended claims the notions 'first' and 'second' are used to distinguish between the probes used in the assay and their respective components. The notions "first" and "second" are not used herein as summations, i.e. it is not so that there can only be a second component when there is also a first component. For reasons of consistency and ease of reference these notions are also used when the embodiment itself does not constitute of two probes or of two components. For instance, a circularizable probe, being only one probe, still contains a first and second target specific section. Likewise, In FIG. 1A, either one of the first and second probe may contain an identifier. In case of the first probe this is depicted as the first identifier and in case of the second probe this is depicted as the second identifier. In case the second probe contains an identifier and the first probe does not, this identifier may referred to in this application as the second identifier without implicating the existence of a first identifier.

A further aspect of the invention relates to kits for use in the methods of the invention comprising the various first, second and or circularizable probes as described herein elsewhere.

EXAMPLE

DNA was isolated from 2 parents and 88 offspring using conventional methods. Parents (2×) and offspring (=4×) were in duplex with different identifiers to test reproducibility. Tags used to distinguish samples or SNP alleles from each other differed at least in 2 nucleotides from any other tag used in the experiments for sample or allele identification, respectively. Quality is being tested throughout the various steps using agarose gels.

Example 1

For each DNA sample a ligation step is performed using probesets designed to detect 30 SNP loci, each comprising 2 alleles. Amplification primer sequences are based on the hybridizing sequences located on the surface of the Solexa high throughput sequencing system. In particular the P5 sequence (PBS2) is situated at the 5' part of the probe hybridising to TS2. The P7 sequence (PBS1) is located at the 3' end of the probe hybridising to TS1.

Adjacent to the 3' end of the P5 sequence, a degenerate sample identifying sequence (SIS) is located comprising of a NNNNN sequence. A GC dinucleotide anchor sequence is following the SIS. Allele identification is made possible by locating a 5 base identifier sequence adjacent to the 3' end of the GC clamp. The reverse complement of the sequencing primer binding site (sPBS) is following the allele identifier sequence (AIS).

The ligation mixture is amplified using P5 and P7 primer sequences in which the P5 primer contains a sample identification sequence and a GC clamp at its 3' end. Products are inspected for yield and appropriate length distribution using agarose detection and subsequently purified using Sephadex™ columns. Concentrations are determined and normalised and pools are created. The pools are subjected to massive parallel sequencing based on Solexa technology comprising bridge amplification and sequencing followed by data analysis to determine the genotypes of the parents and the offspring.

In an alternative scenario the ligation mixture is amplified in a 2-step approach.

A first amplification is performed using P5 and P7 primer sequences without sample identification sequences. Products are inspected for yield and appropriate length distribution using agarose detection. The second PCR uses a P7 primer in conjunction with a P5 primer containing a SIS and a GC clamp at its 3' end. Products are inspected for yield and appropriate length distribution using agarose detection. Concentrations are normalized and samples are pooled. Products are purified by Qiagen columns.

In a second alternative, sequence-based detection is performed using Sanger sequencing after cloning the amplified products into a bacterial plasmid vector with subsequent transformation and colony PCR amplification.

Data analysis yields the genotypes.

Example 2

Sequence-based detection of amplified ligation products was performed using Sanger sequencing.

The experimental sequence involves a ligation step, first amplification using primers without SIS and GC-clamp, second amplification using primers containing SIS and GC-clamp, cloning the products of the second amplification into a bacterial plasmid with subsequent transformation to a bacterial host, single colony PCR amplification and sequence determination by Sanger sequencing.

Maize parental lines B73 and Mo17 were used and sequenced. Over 200 amplified ligation products were sequenced to provide proof-of-principle for sequence-based SNP detection.

Parental lines B73 and Mo17 were selected. Ligation products were prepared using ligation probesets designed to detect 30 SNP loci. Amplification was performed using primers without SIS and GC-clamp. Fragments for cloning were prepared using primers containing SIS and GC-clamp. Cloning was performed using a TOPO TA Cloning® Kit of Invitrogen.

Template fragments for Sanger sequencing were prepared by performing a PCR amplification on single colonies.

Sequence-based ligation markers were identified by extracting 27 bp sequence tags observed adjacent to the sequence primer binding site at different frequencies in B73 and Mo17.

Sequence-based ligation marker data were compared to SNPWave marker scores obtained by conventional SNPWave fingerprinting using length-based detection.

The viability of sequenced-based ligation marker detection was demonstrated using Sanger sequencing, whereby a smaller number of ligation markers is scored using sequence-based detection than on conventional slab gels. However sequencing scale is readily greatly increased using the massive parallel sequencing technology of e.g. Solexa. Marker data comparisons reveal identical segregation patterns between sequence-based detection and slab gel detection.

The invention claimed is:

1. A method for the high throughput detection of a plurality of target nucleotide sequences in one or more samples, comprising the steps of:
   (a) providing for the plurality of target nucleotide sequences, a set of first probes and a set of second probes,
      wherein the probes in the set of first probes comprises a target specific section at its 3' end and a first tag section that is non-complementary to the target nucleotide sequence and comprises a first primer binding sequence,
      wherein the probes in the set of second probes comprises a second target specific section at its 5' end and a second tag section that is non-complementary to the target nucleotide sequence and comprises a second primer binding sequence,
      wherein the first or second tag section, or both, contain(s) an identifier sequence that is located between the respective first or second primer binding sequence and the respective first or second target specific section,
   (b) for each of the target sequences, allowing the first and second target specific section of the respective first probes and second probes to hybridize to the target sequence,
   (c) ligating the first and second probes when the respective target specific sections of the probes are hybridized to essentially adjacent sections on the target sequence to provide ligated probes of same or very similar length,
   (d) optionally, amplifying the ligated probes with a first and a second primer to provide amplicons,
   (e) subjecting the ligated probes or amplicons to high throughput sequencing to determine at least part of the nucleotide sequence, at least including the identifier sequence(s), of the ligated probes or the amplicons,
   (f) identifying the presence of the target nucleotide sequence in the sample by determination of the presence or absence of the identifier sequence in the nucleotide sequence of step (e)
      wherein the identifier does not contain 2 or more identical consecutive bases and/or wherein for two or more samples or for two or more locus/allele combinations, the corresponding identifiers mutually all differ by at least two nucleotides.

2. The method according to claim 1, wherein the first and second probe are replaced by a circularizable probe.

3. The method according to claim 1, wherein the first and second probe are Keylock probes, each comprising a clamp section.

4. The method according to claim 1, wherein the first probe is replaced by a first probe that contains a first target specific section and does not contain a first primer binding sequence, and wherein a compound probe is provided that contains a section that is capable of hybridizing to (part of) the first target specific section of the first probe and a primer binding section, and wherein elongation of the compound probe provides an amplifiable elongated compound probe.

5. The method according to claim 1, wherein the first probe contains a first target specific section, does not contain a primer binding sequence and contains an exonuclease resistant section distal from the point of ligation, wherein the second probe comprises a second target specific section and a second tag section that comprises a first and a second primer binding sequence and a intermittently located identifier.

6. The method according to claim 1, wherein the first and second probes anneal to non-adjacent sections on the target sequence and a third probe is provided that anneals to the target sequence adjacent to, and between, the first and the second target specific section.

7. The method according to claim 1, wherein the first and second probes anneal to non-adjacent sections on the target sequence and a polymerase and nucleotides are provided such that the gap between the first and second probe is filled in.

8. The method according to claim 1, wherein the high throughput sequencing is performed on a solid support.

9. The method according to claim 1, wherein the high throughput sequencing is based on Sequencing-by-Synthesis.

10. The method according to claim 1, wherein the high throughput sequencing comprises the steps of:
   annealing the ligated probes or amplicons to beads, each bead annealing with a single ligated probes or amplicons;
   emulsifying the beads in micro reactors, each water-in-oil microreactor comprising a single bead;
   performing emulsion PCR to amplify ligated probes or amplicons on the surface of beads;
   optionally, selecting/enriching beads containing amplified sequencing-adaptor-ligated fragments;
   loading the beads in wells, each well comprising a single bead; and
   generating a pyrophosphate signal.

11. The method according to claim 1, wherein the high throughput sequencing comprises the steps of:
- annealing the ligated probes or amplicons to beads, each bead annealing with a single ligated probes or amplicons;
- emulsifying the beads in micro reactors, each water-in-oil micro reactor comprising a single bead;
- performing emulsion PCR to amplify ligated probes or amplicons on the surface of beads;
- optionally, selecting/enriching beads containing amplified sequencing-adaptor-ligated fragments;
- loading the beads in wells, each well comprising a single bead; and
- determine the nucleotide sequence of the amplified ligated probes or amplicons using labeled reversible terminator nucleotides.

12. The method according to claim 1, wherein the high throughput sequencing comprises the steps of;
- annealing the ligated probes or amplicons to a surface containing first and second primers or first and second primer binding sequences respectively,
- performing bridge amplification to provide clusters of amplified ligated probes or amplicons,
- determine the nucleotide sequence of the amplified ligated probes or amplicons using labeled reversible terminator nucleotides.

13. The method according to claim 1, wherein the high throughput sequencing comprises the steps of:
- annealing the ligated probes or amplicons to a surface containing first and second primers or first and second primer binding sequences respectively,
- performing bridge amplification to provide clusters of amplified ligated probes or amplicons,
- generating a pyrophosphate signal.

14. The method according to claim 1, wherein the identifier is a sample identifier.

15. The method according to claim 1, wherein the identifier is a combined locus/allele identifier.

16. The method according to claim 1, wherein the identifier comprises a sample identifier and a locus/allele identifier.

17. The method according to claim wherein the identifier is from 1-30 bp.

18. The method according to claim 1, wherein the primer comprises an 3' anchor sequence.

19. The method according to claim 1, wherein for two or more samples or for two or more locus/allele combinations, the identifier sequences are used to genotype the sample(s) for one or more sequences and/or polymorphisms.

20. The method according to claim 1, wherein the identifier is from 2-16 bp.

21. The method according to claim 1, wherein the identifier is from 3-8 bp.

22. The method according to claim 1, wherein the identifier is from 4-6 hp.

23. The method according to claim 19 wherein the polymorphisms are SNPs and/or indels.

* * * * *

UNITED STATES PATENT AND TRADEMARK OFFICE
CERTIFICATE OF CORRECTION

| | |
|---|---|
| PATENT NO. | : 8,460,866 B2 |
| APPLICATION NO. | : 12/281193 |
| DATED | : June 11, 2013 |
| INVENTOR(S) | : Van Eijk et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 113 days.

Signed and Sealed this
Sixth Day of January, 2015

Michelle K. Lee
*Deputy Director of the United States Patent and Trademark Office*